United States Patent
Konry et al.

(10) Patent No.: US 10,928,382 B2
(45) Date of Patent: Feb. 23, 2021

(54) MICROFLUIDIC DEVICE AND METHOD FOR ANALYSIS OF TUMOR CELL MICROENVIRONMENTS

(71) Applicant: Northeastern University, Boston, MA (US)

(72) Inventors: Tania Konry, Boston, MA (US); Noa Cohen, Newton, MA (US); Pooja Sabhachandani, Boston, MA (US)

(73) Assignee: Northeastern University, Boston, MA (US)

( * ) Notice: Subject to any disclaimer, the term of this patent is extended or adjusted under 35 U.S.C. 154(b) by 131 days.

(21) Appl. No.: 15/321,386

(22) PCT Filed: Jun. 26, 2015

(86) PCT No.: PCT/US2015/038063
§ 371 (c)(1),
(2) Date: Dec. 22, 2016

(87) PCT Pub. No.: WO2015/200832
PCT Pub. Date: Dec. 30, 2015

(65) Prior Publication Data
US 2017/0199173 A1    Jul. 13, 2017

Related U.S. Application Data

(60) Provisional application No. 62/017,318, filed on Jun. 26, 2014.

(51) Int. Cl.
*G01N 33/50* (2006.01)
*B01L 3/00* (2006.01)
(Continued)

(52) U.S. Cl.
CPC ...... *G01N 33/5011* (2013.01); *B01L 3/50273* (2013.01); *B01L 3/502761* (2013.01);
(Continued)

(58) Field of Classification Search
CPC .................................. G01N 33/50; B01L 3/00
(Continued)

(56) References Cited

U.S. PATENT DOCUMENTS 4,391,909 A    7/1983 Lim
9,664,619 B2 *    5/2017 Boehm ............. B01L 3/502784
(Continued)

FOREIGN PATENT DOCUMENTS

WO    2012148684 A1    11/2012
WO    2014052835 A1    4/2014

OTHER PUBLICATIONS

Riccalton-Banks, L. et al, Tissue Engineering 2003, 9, 401-410.*
(Continued)

*Primary Examiner* — Arlen Soderquist
(74) *Attorney, Agent, or Firm* — Verrill Dana, LLP

(57) ABSTRACT

A microfluidic device provides high throughput generation and analysis of defined three-dimensional cell spheroids with controlled geometry, size, and cell composition. The cell spheroids of the invention mimic tumor microenvironments, including pathophysiological gradients, cell composition, and heterogeneity of the tumor mass mimicking the resistance to drug penetration providing more realistic drug response. The device is used to test the effects of antitumor agents.

17 Claims, 13 Drawing Sheets

(51) Int. Cl.
<table>
<tr><td>C12M 1/12</td><td>(2006.01)</td></tr>
<tr><td>C12M 3/06</td><td>(2006.01)</td></tr>
<tr><td>C12M 1/00</td><td>(2006.01)</td></tr>
<tr><td>C12N 5/09</td><td>(2010.01)</td></tr>
</table>

(52) U.S. Cl.
CPC ....... *B01L 3/502784* (2013.01); *C12M 23/16* (2013.01); *C12M 25/01* (2013.01); *C12M 25/14* (2013.01); *C12M 29/10* (2013.01); *C12N 5/0693* (2013.01); *G01N 33/5044* (2013.01); *B01L 2200/0647* (2013.01); *B01L 2200/0668* (2013.01); *B01L 2200/0673* (2013.01); *B01L 2300/087* (2013.01); *B01L 2300/0816* (2013.01); *B01L 2300/0864* (2013.01); *B01L 2300/0867* (2013.01); *B01L 2300/0883* (2013.01); *B01L 2300/168* (2013.01); *B01L 2300/18* (2013.01); *B01L 2400/0478* (2013.01); *C12N 2502/11* (2013.01); *C12N 2513/00* (2013.01); *C12N 2533/74* (2013.01)

(58) Field of Classification Search
USPC .......................................... 422/502; 436/63
See application file for complete search history.

(56) References Cited

U.S. PATENT DOCUMENTS

| | | | |
|---|---|---|---|
| 2006/0051329 A1* | 3/2006 | Lee ........................ | B01F 3/0807 424/93.7 |
| 2007/0172943 A1* | 7/2007 | Freedman ............... | C12M 25/14 435/293.1 |
| 2009/0035770 A1* | 2/2009 | Mathies ............ | B01L 3/502753 435/6.19 |
| 2009/0041825 A1 | 2/2009 | Kotov | |
| 2009/0068170 A1* | 3/2009 | Weitz .................... | G01N 33/505 424/130.1 |
| 2010/0021984 A1* | 1/2010 | Edd ......................... | C12N 11/04 435/174 |
| 2010/0124759 A1* | 5/2010 | Wang ................ | B01L 3/502715 435/28 |
| 2010/0137163 A1* | 6/2010 | Link ................... | B01F 13/0071 506/16 |
| 2010/0163109 A1* | 7/2010 | Fraden ............. | B01L 3/502715 137/1 |
| 2010/0255059 A1* | 10/2010 | Marquez ................. | A61F 2/022 424/424 |
| 2011/0081664 A1* | 4/2011 | Forbes ................... | C12M 23/22 435/7.23 |
| 2011/0190146 A1* | 8/2011 | Boehm ................... | B01L 7/525 506/7 |
| 2011/0306110 A1 | 12/2011 | Takeuchi et al. | |
| 2012/0222748 A1* | 9/2012 | Weitz .................... | B01F 3/0807 137/1 |
| 2012/0258487 A1* | 10/2012 | Chang .................... | C12N 15/10 435/34 |
| 2013/0016341 A1* | 1/2013 | Liu ....................... | G01N 21/05 356/128 |
| 2013/0035257 A1 | 2/2013 | Yu et al. | |
| 2013/0052648 A1* | 2/2013 | Yarmush .............. | C12Q 1/6804 435/6.12 |
| 2013/0130301 A1 | 5/2013 | Yoon et al. | |
| 2013/0210680 A1* | 8/2013 | Derda ................. | C12N 15/1037 506/26 |
| 2013/0224860 A1 | 8/2013 | Mohapatra et al. | |
| 2013/0236901 A1* | 9/2013 | Potier ................ | G01N 35/1009 435/6.12 |
| 2013/0244906 A1* | 9/2013 | Collins .............. | G01N 21/6486 506/12 |
| 2014/0127290 A1 | 5/2014 | He et al. | |
| 2014/0212910 A1* | 7/2014 | Bhatia .................. | C12N 5/0012 435/29 |
| 2016/0115436 A1* | 4/2016 | Aijian .................... | C12M 23/16 435/173.9 |
| 2017/0056331 A1* | 3/2017 | Stone .................. | A61K 31/085 |
| 2017/0058264 A1* | 3/2017 | Mohapatra ........... | C12N 5/0693 |
| 2018/0371415 A1* | 12/2018 | Vunjak-Novakovic ...................... | C12N 5/0654 |

OTHER PUBLICATIONS

Nie, Z. et al, Journal of the American Chemical Society 2005, 127, 8058-8063.*
Oh, H.-J. et al, Journal of Micromechanics and Microengeering 2006, 16, 285-291.*
Choi, C.-H. et al, Biomedical Microdevices 2007, 9, 855-862.*
Um, E. et al, Microfluidics and Nanofluidics 2008, 5, 541-549.*
Koster, S. et al, Lab on a Chip 2008, 8, 1110-1115.*
Edd, J. F. et al, Lab on a Chip 2008, 8, 1262-1264.*
Kim, C. et al, Lab on a Chip 2009, 9, 1294-1297.*
Hirschhaeuser, F. et al, Journal of Biotechnology 2010, 148, 3-15.*
Okuyama, T. et al, Journal of Bioscience and Bioengineering 2010, 110, 572-576.*
Kim, C. et al, Lab on a Chip 2011, 11, 246-252.*
Kumachev, A. et al, Biomaterials 2011, 32, 1477-1483.*
Kim, C. et al, Lab on a Chip 2012, 12, 4135-4142.*
LaBarbera, D. V. et al, Expert Opinion on Drug Discovery 2012, 7, 819-830.*
Achilli, T.-M. et al, Expert Opinion on Biological Therapy 2012, 12, 1347-1360.*
Yoon, S. et al, Lab on a Chip 2013, 13, 1522-1528.*
Allazetta, S. et al, Biomacromolecules 2013, 14, 1122-1131.*
Golberg, A. et al, Microchimica Acta 2013, 180, 855-860.*
Koury, T. et al, Scientific Reports 2013, 3, paper 3179, 5 pages.*
Chan, H. F. et al, Scientific Reports 2013, 3, paper 3462, 8 pages.*
Golberg, A. et al, PLOS One 2014, 9, paper e86341, 9 pages.*
Durek, C. et al, Journal of Urology 1999, 162, 600-605.*
Heimdal, J.-H. et al, Scandinavian Journal of Immunology 2000, 51, 271-278.*
Heimdal, J.-H. et al, Scandinavian Journal of Immunology 2001, 53, 162-170.*
Takayama, S. et al, Advanced Materials 2001, 13, 570-574.*
Wartenberg, M. et al, FASEB Journal 2001, 15, 995-1005.*
Kawai, K. et al, Cytotechnology 2001, 37, 31-40.*
Wartenberg, M. et al, Laboratory Investigation 2003, 83, 87-98.*
Nie, Z. et al, Journal of the American Chemical Society 2006, 128, 9408-9412.*
Zhang, H. et al, Journal of the American Chemical Society 2006, 128, 2205-12210.*
Liu, K. et al, Langmuir 2006, 22, 9453-9457.*
Torisawa, Y. et al, Lab on a Chip 2007, 7, 770-776.*
Karp, J. M. et al, Lab on a Chip 2007, 7, 786-794.*
Workman, V. L. et al, Macromolecylar Rapid Communications 2008, 29, 165-170.*
Kross, K. W. et al, Scandinavian Journal of Immunology 2008, 67, 392-399.*
Paduch, R. et al, In Vitro Cellular & Developmental Biology—Animal 2009, 45, 371-377.*
Gartner, Z. J. et al, Proceedings of the National Academy of Sciences of the United States of America 2009, 106, 4606-4610.*
Zhang, B. et al, Biomedical Microdevices 2009, 11, 1233-1237.*
Mantovani, A. et al, Cytokine & Growth Factor Reviews 2010, 21, 27-39.*
Hannig, M. et al, Journal of Cellular and Molecular Medicine 2010, 14, 303-312.*
Cheng, H. et al, ACS Nano 2010, 4, 625-631.*
Liu,, T. et al, Lab on a Chip 2010, 10, 1671-1677.*
Kang, E. et al, Lab on a Chip 2010, 10, 1856-1861.*
Tumarkin, E. et al, Integrative Biology 2011, 3, 653-662.*
Franco, O. E. et al, Cancer Research 2011, 71, 1272-1282.*
Li, C. Y. et al, Lab on a Chip 2011, 11, 2967-2975.*
Chin, L. K. et al, 2012 IEEE 25th International Conference on Micro Electro Mechanical Systems (MEMS) 2012, 808-811.*
Kim, J. et al, British Journal of Haematology 2012, 158, 336-346.*

(56) References Cited

OTHER PUBLICATIONS

Yamada, M. et al, Biomaterials 2012, 33, 8304-8315.*
Juul, S. et al, ACS Nano 2012, 6, 10676-10683.*
Mazzitelli, S. et al, Advanced Drug Delivery Reviews 2013, 65, 1533-1555.*
Agarwal, P. et al, Lab on a Chip 2013, 13, 4525-4533.*
Yeh, C.-H. et al, Journal of Micromechanics and Microengineering 2013, 23, paper 125025, 11 pages.*
Akbari, S. et al, Microfluidics and Nanofluidics 2014, 16, 773-777.*
Sugiura, S. et al, Biomaterials 2005, 26, 3327-3331.*
Zhang, H. et al, Macromolecular Rapid Communications 2007, 28, 527-538.*
Clausell-Tormos, J. et al, Chemistry & Biology 15, 427-437.*
Schmitz, C. H. J. et al, Lab on a Chip 2009, 9, 44-49.*
Kamei, K.-I. et al, Lab on a Chip 2009, 9, 555-563.*
Xu, Q. et al, Small 2009, 5, 1575-1581.*
Khoury, M. et al, Biomedical Microdevices 2010, 12, 1001-1008.*
Kim, C. et al, Lab on a Chip 2011, 11, 874-882.*
Ho, Y.-P. et al, Nano Letters 2011, 11, 2178-2182.*
Pan, J. et al, Integrative Biology 2011, 3, 1043-1051.*
Rossow, T. et al, Journal of the American Chemical Society 2012, 134, 4983-4989.*
Velasco, D. et al, Small 2012, 8, 1633-1642.*
Wang, Y. et al, Analyst 2014, 139, 2449-2458.*
Huebner, A. et al, Lab on a Chip 2009, 9, 692-698.*
Ramji, R, et al, Journal of Biosensors and Bioelectronics 2013, S12 (special issue), 4 pages.*
Gomez-Sjoberg R et al. Versatile, Fully Automated, Microfluidic Cell Culture System. Anal. Chem. 2007,79, 8557-8563.
Konry T et al. Droplet-based microfluidic platforms for single T cell secretion analysis of IL-10 cytokine. Biosens Bioelectron. Jan. 15, 2011; 26(5): 2707-2710.
Hsiao A et al. Microfluidic system for formation of PC-3 prostate cancer co-culture spheroids. Biomaterials 30 (2009) pp. 3020-3027.
Lewis C et al. Microfluidic Fabrication of Hydrogel Microparticles Containing Functionalized Viral Nanotemplates. Langmuir 2010, 26(16), 13436-13441.
Yu B. J. Preparation of monodisperse PEG hydrogel composite microspheres via microfluidic chip with rounded channels. Micromech. Microeng. 23 (2013) 095016.
Dai X et al. Free radical polymerization of poly(ethylene glycol) diacrylate macromers: Impact of macromer hydrophobicity and initiator chemistry on polymerization efficiency. Acta Biomaterialia 7 (2011) 1965-1972.
Rezende R et al. Experimental Characterisation of the Alginate Gelation Process for Rapid Prototyping. Chem. Eng. Trans. 11, pp. 509-514 (2007).
Orive G et al. Biocompatibility of alginate—poly-L-lysine microcapsules for cell therapy. Biomaterials 27 (2006) 3691-3700.
Tibbitt M. et al. Hydrogels as Extracellular Matrix Mimics for 3D Cell Culture. Biotechnology and Bioengineering, vol. 103, No. 4, Jul. 1, 2009, p. 655-663.
Dhiman H et al. Three-dimensional chitosan scaffold-based MCF-7 cell culture for the determination of the cytotoxicity of tamoxifen. Biomaterials 26 (2005) 979-986.
Shoulders M et al. Collagen structure and stability. Annu Rev Biochem. 2009 ; 78: 929-958.
Sang L et al. Fabrication and evaluation of biomimetic scaffolds by using collagen—alginate fibrillar gels for potential tissue engineering applications. Materials Science and Engineering C 31 (2011) 262-271.
Kim G et al. Coaxial structured collagen—alginate scaffolds: fabrication, physical properties, and biomedical application for skin tissue regeneration. J. Mater. Chem., 2011, 21, 6165-6172.
Chen W et al. Microencapsulated 3-Dimensional Sensor for the Measurement of Oxygen in Single Isolated Pancreatic Islets. PLoS ONE 7(3): e33070.
Alessandri K et al. Cellular capsules as a tool for multicellular spheroid production and for investigating the mechanics of tumor progression in vitro. PNAS. vol. 110, No. 37, pp. 14843-14848.
Sakai Y et al. Detachably assembled microfluidic device for perfusion culture and post-culture analysis of a spheroid array. Biotechnol. J. 2014, 9, 971-979.
Ziolkowska K et al. Long-term three-dimensional cell culture and anticancer drug activity evaluation in a microfluidic chip. Biosensors and Bioelectronics 40(2013) 68-74.
Wu L et al. Microfluidic self-assembly of tumor spheroids for anticancer drug discovery. Biomed Microdevices (2008) 10:197-202.
Lan S. Alginate based 3D hydrogels as an in vitro co-culture model platform for the toxicity screening of new chemical entities. Toxicology and Applied Pharmacology 256 (2011) 62-72.
Kievit F et al. Chitosane alginate 3D scaffolds as a mimic of the glioma tumor microenvironment. Biomaterials 31 (2010) 5903-5910.
Chen L. The enhancement of cancer stem cell properties of MCF-7 cells in 3D collagen scaffolds for modeling of cancer and anticancer drugs. Biomaterials 33 (2012) 1437-1444.
Tan W-H et al. Monodisperse Alginate Hydrogel Microbeads for Cell Encapsulation. Adv. Mater. 2007, 19, 2696-2701.
Yu L et al. Droplet-based microfluidic system for multicellular tumor spheroid formation and anticancer drug testing. Lab Chip, 2010, 10, 2424-2432.

* cited by examiner

MICROFLUIDIC DEVICE AND METHOD FOR ANALYSIS OF TUMOR CELL MICROENVIRONMENTS

BACKGROUND

Numerous cancer model systems are now available to investigate disease mechanisms and to screen therapies. However, current preclinical tools to investigate cancer biology and potential tumor treatments still have significant problems. To investigate tumor cell biology and drug efficiency, it would be advantageous to utilize an ex vivo cell culture system that mimics the microenvironment of a tumor. Available two-dimensional (2D) tissue culture models and monolayer cultures lack the realistic complexity of tumor microenvironments and cannot represent tumor heterogeneity or the resistance to drug penetration, which are critical parameters. The tumor microenvironment plays a critical role in cell differentiation, growth and metastatic processes and greatly impacts therapeutic efficacy. Secretory growth factors from cancer-associated fibroblasts have been shown to stimulate proliferation of tumor cells and appear to play a crucial role in disease progression and establishment and maintenance of the tumor microenvironment. Additional features of tumor microenvironments include evasion by components of the immune system. It has been suggested that the presence of immune cells allows tumor cells to be more aggressive and that, without the presence of immune cells, cancer stem cells may not efficiently progress.

Continuous progress in tissue engineering has made possible the development of various 3D scaffolds and bioreactor systems, which have improved the diversity, fidelity, and capacity of culture models in cancer research. Among the 3D in vitro culture systems that have been developed, tumor spheroid or sphere cultures are becoming a popular approach to obtain and maintain the functional phenotype of human tumor cells. Interestingly, many recent reports state that CSC populations are particularly and/or exclusively maintained in sphere culture. However, today only a small number of cell sphere systems are sufficiently well characterized to resemble the tumor-like 3D cytoarchitecture as well as simulate the pathophysiological micro-milieu and tumor cell responses of the in vivo tumor state. Unfortunately, some so-called spheres and even spheroids described in the literature are no more than loose aggregates of cancer cells that easily detach, cannot be manipulated or transferred, and may lack both cell—cell and cell—matrix interactions, but also lack a true spherical geometry.

SUMMARY OF THE INVENTION

The invention provides a microfluidic platform for high throughput generation and analysis of clearly defined 3D cell spheroids with uniform geometry and versatility in terms of the spheroid sizes and cell composition. The cell spheroids of the invention resemble the tumor microenvironment, including pathophysiological gradients, cell composition and heterogeneity of the tumor mass mimicking the resistance to drug penetration providing more realistic drug response.

One aspect of the invention is a microfluidic device for the formation and analysis of cell spheroids. The device includes: a first inlet for an oil, a second inlet for a first aqueous suspension of cells, and a third inlet for a polymerization mediator; a nozzle formed by a T-shaped intersection of two or more of the first, second, and third microchannels; and an incubation chamber containing a plurality of microchambers configured in a two-dimensional array. The first inlet is fluidically connected to a first microchannel; the second inlet is fluidically connected to a second microchannel; and the third inlet is fluidically connected to a third microchannel. The nozzle is capable of producing aqueous droplets suspended in the oil; the aqueous droplets contain the cells and the polymerization mediator. The incubation chamber is fluidically connected to the nozzle, and is capable of accepting and delivering the aqueous droplets individually into the microchambers.

Another aspect of the invention is a cell spheroid comprising two or more cell types adhered to an essentially spherical polymer scaffold.

Still another aspect of the invention is a kit including the microfluidic device described above, together with one or more reagents, cells, or polymers, and instructions for use.

Yet another aspect of the invention is a method of making a plurality of cell spheroids. The method includes the steps of: (a) providing the microfluidic device described above, together with an oil, a first cell suspension containing a polymer precursor, and a polymerization mediator; (b) flowing the oil, first cell suspension, and polymerization mediator into the first, second, and third inlets, respectively, whereby aqueous droplets suspended in the oil are formed by the nozzle of the microfluidic device, the droplets containing cells of the first cell suspension, the polymer precursor, and the polymerization mediator; (c) allowing the polymer precursor to polymerize to form polymer scaffolds in the aqueous droplets, whereby a cell spheroid is formed in each droplet; and (d) distributing the cell spheroids into the microchambers of the microfluidic device.

Still another aspect of the invention is a method of monitoring a cell spheroid for the effect of a test substance. The method includes the steps of: (a) providing a microfluidic device as described above, wherein the device contains an array of cell spheroids in the incubation chamber of the device; (b) perfusing the incubation chamber with an aqueous solution containing the test substance; and (c) monitoring the cell spheroids.

Further embodiments of the invention are summarized in the following list of items.

1. A microfluidic device for the formation and analysis of cell spheroids, the device comprising:
    a first inlet for an oil, a second inlet for a first aqueous suspension of cells, and a third inlet for a polymerization mediator; the first inlet fluidically connected to a first microchannel, the second inlet fluidically connected to a second microchannel, and the third inlet fluidically connected to a third microchannel;
    a nozzle formed by a T-shaped intersection of two or more of the first, second, and third microchannels, the nozzle capable of producing aqueous droplets suspended in the oil, the aqueous droplets comprising the cells and the polymerization mediator; and
    an incubation chamber comprising a plurality of microchambers configured in a two-dimensional array, the incubation chamber fluidically connected to the nozzle and capable of accepting and delivering said aqueous droplets individually into said microchambers.
2. The microfluidic device of item 1, further comprising a fourth inlet for a second aqueous suspension of cells, the fourth inlet fluidically connected to a fourth microchannel, the fourth microchannel fluidically connected to the second microchannel at a junction capable of forming a cell mixture comprising cells from the first and second cell suspensions.

3. The microfluidic device of item 2, further comprising a fifth inlet for a third aqueous suspension of cells, the fifth inlet fluidically connected to a fifth microchannel, the fifth microchannel fluidically connected to the second and/or fourth microchannels such that a cell mixture is formed, the cell mixture comprising cells from the first, second, and third cell suspensions.
4. The microfluidic device of any of the preceding items, further comprising an optically transparent window covering the microchambers, wherein the device is configured to permit light microscopic observation of cells in the microchambers.
5. The microfluidic device of any of the preceding items, further comprising one or more liquid perfusion pathways for perfusion of one or more of said microchambers.
6. The microfluidic device of item 5, wherein each microchamber can be separately perfused.
7. The microfluidic device of item 5, wherein one or more groups of microchambers can be separately perfused.
8. The microfluidic device of any of the preceding items, further comprising one or more additional inlets, one or more additional microchannels, one or more outlets, and/or one or more valves, pumps, mixing zones, incubation chambers, vacuum channels, ports, heaters, vents, reservoirs, reagents, or waste chambers.
9. The microfluidic device of any of the preceding items, wherein the microchambers each have a diameter in the range from about 70 microns to about 900 microns.
10. The microfluidic device of any of the preceding items, wherein the microchambers are configured as substantially spherical spaces connected via microchannels.
11. The microfluidic device of item 10, wherein the microchannels connected to the microchambers have a diameter in the range from about 50 microns to about 400 microns.
12. The microfluidic device of item 10, wherein the diameter of the microchannels is less than the diameter of the microchambers.
13. The microfluidic device of item 9, wherein the microchambers are configured as docking stations within the incubation chamber.
14. The microfluidic device of any of the preceding items, further comprising one or more cell spheroids disposed in one or more of said microchambers.
15. The microfluidic device of item 14, wherein the cell spheroids each comprise two or more different cell types.
16. The microfluidic device of any of items 14-15, wherein the cell spheroids comprise a polymer scaffold.
17. The microfluidic device of any of the preceding items which is fabricated from polydimethylsiloxane and glass.
18. A cell spheroid comprising two or more cell types adhered to an essentially spherical polymer scaffold.
19. The cell spheroid of item 18, comprising three or more cell types.
20. The cell spheroid of item 19, wherein the three cell types are a tumor cell or model therefor, an immune cell, and a stromal cell.
21. The cell spheroid of item 18 or item 19, wherein the polymer is selected from the group consisting of alginate, agarose, collagen, chitosan, and polyethylene glycol.
22. The cell spheroid of any of items 18-21, further comprising a cell adhesion peptide.
23. The cell spheroid of any of items 18-22 having a diameter in the range from about 50 microns to about 900 microns.
24. The cell spheroid of any of items 18-23 comprising a necrotic core.
25. A plurality of the cell spheroids of any of items 18-24 configured as an array.
26. The plurality of cell spheroids of item 25, wherein the array is encased in a microfluidic device capable of incubating and perfusing the cell spheroids.
27. A kit comprising a microfluidic device of any of items 1-17; one or more reagents, cells, or polymers; and instructions for use.
28. A method of making a plurality of cell spheroids, the method comprising the steps of:
    (a) providing the microfluidic device of item 1, an oil, a first cell suspension comprising a polymer precursor, and a polymerization mediator;
    (b) flowing the oil, first cell suspension, and polymerization mediator into the first, second, and third inlets, respectively, whereby aqueous droplets suspended in the oil are formed by the nozzle of the microfluidic device, the droplets comprising cells of the first cell suspension, the polymer precursor, and the polymerization mediator;
    (c) allowing the polymer precursor to polymerize to form polymer scaffolds in the aqueous droplets, whereby a cell spheroid is formed in each droplet; and
    (d) distributing the cell spheroids into the microchambers of the microfluidic device.
29. The method of item 28, further comprising:
    (e) interrupting the flow of oil in the cell incubation chamber of the microfluidic device and flowing an aqueous solution into the incubation chamber, whereby the cell spheroids are washed.
30. The method of item 29, further comprising:
    (f) initiating a flow of cell culture medium through the incubation chamber; and
    (g) placing the device into an environment suitable for survival and/or growth of the cells in the cell spheroids.
31. The method of item 30, further comprising:
    (h) allowing the cells in the cell spheroids to proliferate.
32. The method of any of items 28-31, further comprising providing in step (a) a second cell suspension and a microfluidic device that further comprises a fourth inlet fluidically connected to a fourth microfluidic channel which is fluidically connected to the second microchannel at a junction capable of forming a cell mixture comprising cells from the first and second cell suspensions; whereby the second cell suspension mixes with the first cell suspension in step (b), and whereby the formed aqueous droplets comprise a mixture of cells from the first and second cell suspensions.
33. The method of any of items 28-31, further comprising providing in step (a) second and third cell suspensions and a microfluidic device that further comprises a fourth and fifth inlets fluidically connected to fourth and fifth microfluidic channels, respectively, which are fluidically connected to the second microchannel at a junction capable of forming a cell mixture comprising cells from the first, second, and third cell suspensions; whereby the second and third cell suspensions mix with the first cell suspension in step (b), and whereby the formed aqueous droplets comprise a mixture of cells from the first, second, and third cell suspensions.

34. The method of any of items 28-33, wherein the polymer scaffolds comprise one or more polymers selected from the group consisting of alginate, agarose, collagen, chitosan, and polyethylene glycol.

35. The method of any of items 28-34, wherein the first cell suspension in (a) further comprises a cell adhesion peptide.

36. The method of any of items 28-35, wherein the polymerization mediator in (a) is a solution containing a divalent or trivalent cation.

37. The method of any of items 28-36, wherein the flowing of oil in (b) is at a rate in the range from about 150 µL/hr to about 500 µL/hr, wherein the flowing of first cell suspension in (b) is at a rate in the range from about 75 µL/hr to about 150 µL/hr, wherein an alginate scaffold is formed in (c), and wherein the polymerization mediator is a 0.1 to 1 M calcium salt solution and its flowing in (b) is at a rate in the range from about 1 µL/hr to about 20 µL/hr.

38. The method of any of items 28-37, wherein the first cell suspension in (a) comprises alginate at a concentration from about 0.25% w/v to about 2% w/v.

39. The method of any of items 28-38, wherein the oil comprises a vegetable oil, a silicone oil, or a mineral oil.

40. A method of monitoring a cell spheroid for the effect of a test substance, the method comprising the steps of:
    (a) providing the microfluidic device of item 14, wherein the device comprises an array of cell spheroids in the incubation chamber of the device;
    (b) perfusing the incubation chamber with an aqueous solution comprising the test substance; and
    (c) monitoring the cell spheroids.

41. The method of item 40, wherein the step of monitoring comprises determining a change in survival, growth, and/or proliferation of cells within the cell spheroids.

42. The method of any of items 40-41, wherein the cell spheroids comprise tumor cells.

43. The method of any of items 40-42, wherein the test substance is an antitumor agent.

BRIEF DESCRIPTION OF THE DRAWINGS

FIGS. 6A and 6B show spheroids of adriamycin resistant MCF7 cells incubated without (FIG. 6A) and with (FIG. 6B) 12.8 µM doxorubicin. FIG. 6A is after 96 hr incubation; FIG. 6B is after 48 hr incubation with doxorubicin. FIGS. 6C and 6D show spheroids of adriamycin sensitive MCF7 cells incubated without (FIG. 6C) and with (FIG. 6D) 12.8 µM doxorubicin. FIG. 6C is after 96 hr incubation; FIG. 6D is after 48 hr incubation with doxorubicin. FIGS. 6E and 6F show spheroids of adriamycin sensitive MDF7 cells co-cultured with HS5 bone marrow fibroblasts. The spheroids were incubated without (FIG. 6E) and with (FIG. 6F) 12.8 µM doxorubicin. FIG. 6E is after 96 hr incubation; FIG. 6F is after 48 hr incubation with doxorubicin.

FIG. 7A shows changes in viability between 2D monolayers and 3D spheroids of MCF7 adriamycin resistant cells upon treatment with varying concentrations of doxorubicin (800 nM to 12800 nM). FIG. 7B shows changes in viability between 2D monolayers and 3D spheroids of MCF7 adriamycin sensitive cells upon treatment with varying concentrations of doxorubicin (800 nM to 12800 nM). FIG. 7C compares the viability of MCF7 adriamycin resistant and sensitive cells as 3D spheroids upon treatment with varying concentrations of doxorubicin (800 nM to 12800 nM). FIG. 7D compares cell viability in 3D MCF7 adriamycin sensitive and MCF7-HS5 co-cultured spheroids upon treatment with doxorubicin at 3200 nM and 12800 nM.

DETAILED DESCRIPTION OF THE INVENTION

Figure 1A:
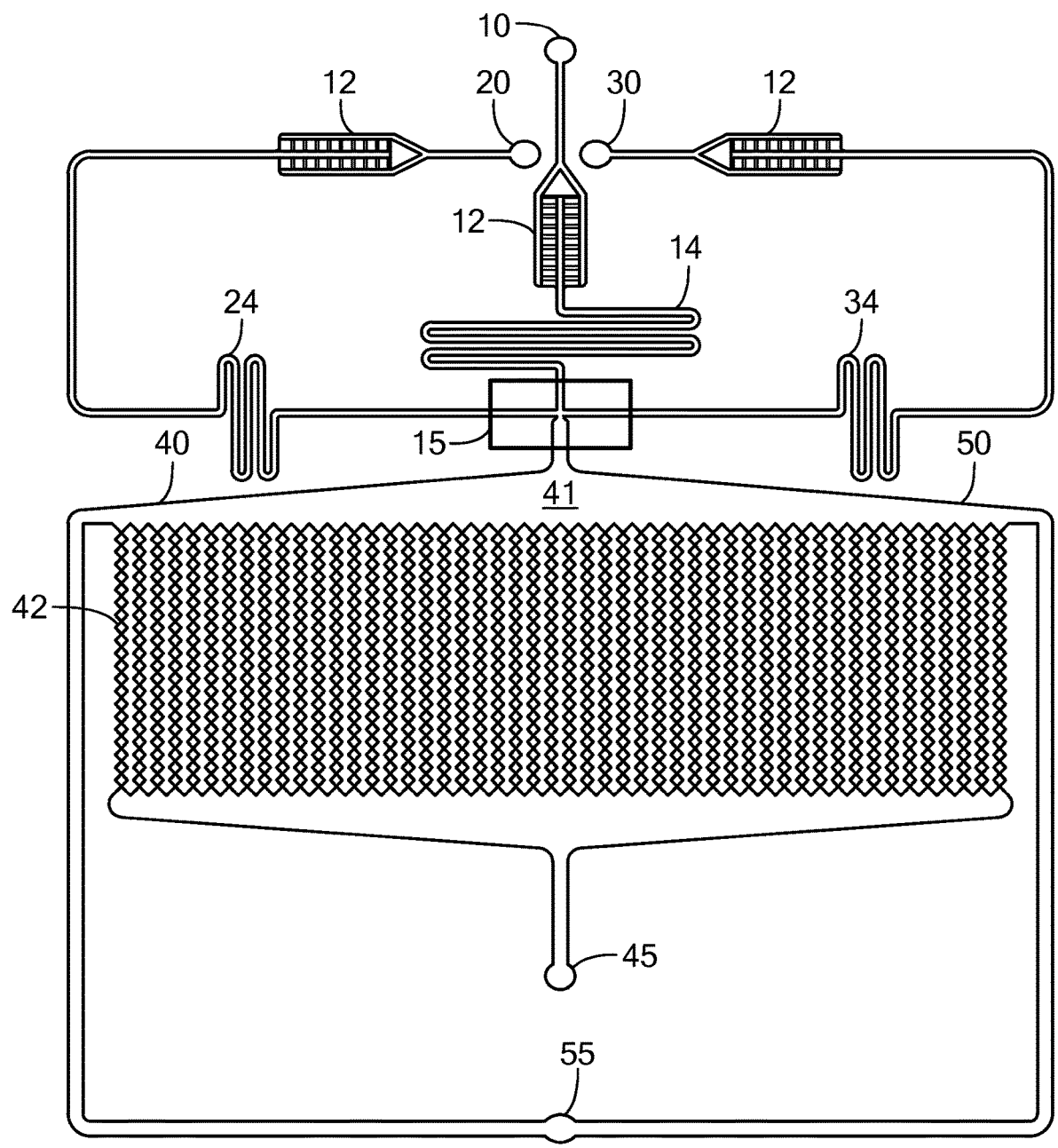
FIGS. 1A-1C show different embodiments of the microfluidic device of the invention.

The present invention provides devices and methods for preparing and analyzing three-dimensional (3D) cell spheroids for investigation of cell microenvironments, including cell-cell and cell-extracellular matrix interactions and the effects of pharmaceutical and biological agents on cell viability, growth, and development. The invention is particularly useful for screening antitumor agents and their combinations using a combination of co-cultured cell types in a controlled 3D configuration that realistically mimics the ability of chemotherapeutic agents to attack small early stage metastatic growths in a cancer patient.

As used herein, "cell spheroid" refers to any generally round collection of cells bound to a substantially spherical polymer scaffold. The size of a cell spheroid can vary in the range from about 50 microns (µm) to about 900 microns in diameter, and is substantially determined and delimited by the size of the polymer scaffold to which the cells are bound. The methods of the invention, described below, permit cell spheroid size to be varied by the design of the microfluidic device used to produce them. Larger cell spheroids having a diameter of about 500 microns or more can develop a necrotic center due to the lack of availability of nutrients or buildup of waste products in the core. In general, larger cell spheroids have three layers: a core which may be necrotic, a middle layer of viable and substantially stationary cells, and an outer layer of migrating cells.

The strategy of forming cell spheroids according to the present invention is to first form a series of aqueous droplets in an oil (such as mineral oil, silicone oil, or a vegetable oil, the oil optionally including a low concentration of a surfactant to improve flow characteristics) using a nozzle containing a T-shaped junction in a microfluidic device (i.e., a device for handling fluids that has at least one channel of diameter in the range from 1 to 999 microns). The droplets are substantially spherical, and their aqueous contents include a suspension of one or more types of individual cells and an initially non-polymerized form of a polymer suitable for mimicking fibrous elements of the extracellular matrix of a mammalian tissue. The droplets may also include a polymerization mediator or catalyst, which is a chemical agent that reacts with a polymer precursor in the droplet to form a 3D polymer scaffold within the droplet, such as a microbead composed of an essentially spherical network of fibers. The droplets as formed also include one or more cells or mixtures of different types of cells. The cells can be any type of cell including, for example, tumor cells (including tumor stem cells and model tumor cells), cells of a cell line or culture, cells from a patient, immune cells such as lymphocytes or macrophages, stromal cells, or fibroblasts. The cells preferably adhere to the polymer scaffold and grow, differentiate, and/or proliferate within the droplet to form a cell spheroid.

An exemplary polymer is alginate, which can be supplied as a soluble solution of sodium alginate, into which is mixed, and the nozzle of the microfluidic device during droplet formation, a $CaCl_2$ solution which serves as polymerization mediator. The $Ca^{2+}$ ions (or any other suitable divalent or trivalent cation that promotes alginate polymerization) cause the formation of a network of polymerized alginate fibers within the droplets within minutes after mixing at the nozzle, resulting in formation of a polymer scaffold for cell attachment. Many other suitable polymers and corresponding polymerization mediators can be used. For example, the polymer can be formed from collagen (polymerized by a pH elevation), agarose (polymerized by a temperature reduction), polyethylene glycol (PEG, polymerized using UV light directed at an appropriate zone of the microfluidic device), or chitosan.

Sodium alginate (a salt of alginic acid, a naturally occurring polysaccharide) can be utilized for cell encapsulation and has advantages including biocompatibility, mechanical resistance, formation of a hydrogel at physiological pH, and optimal pore size for nutrient and gas exchange. Alginate can be modified chemically or physically, e.g., modified with cell adhesion peptides such as GRGDY to facilitate cellular interaction and adhesion. The concentration range of alginate for cell encapsulation is preferably 0.25%-2% w/v in complete cell growth media.

Polyethylene glycol (PEG) is a crosslinked polyether that has good biocompatibility and low immunogenicity. Many PEG derivatives capable of polymerization by free radical methods are available. For example, PEG can be functionalized with acrylate and methacrylate groups at the chain ends. 2-hydroxy-2-methylpropiophenone can be used as photoinitiator for polymerization by UV light provided and focused through a microscope. The concentration range of PEG for cell encapsulation is preferably 0.25%-10% w/v in complete cell growth media.

Agarose is a linear polysaccharide consisting of alternating residues of β-1,3-linked-D-galactose and α-1,4-linked 3,6-anhydro-L-galactose. Aqueous agarose solutions form gels upon cooling, due to the aggregation of double helices formed by the physical entanglement of anhydro bridges on the individual molecules. Solutions of low-gelling temperature agarose are particularly useful for cell encapsulation. At moderately high concentrations, they are liquid at a temperature of 37° C., and below 20° C. they gel, and upon heating to 37° C. they remain gel-like. The concentration of agarose used for cell encapsulation is preferably 0.5%-10% w/v in complete cell growth media.

Collagen enhances cellular activities including attachment and proliferation through interactions between the Arg-Gly-Asp (RGD) domains of collagen and the integrin receptors in the cell membrane. In addition, collagen is a major component of the extracellular matrix, and has low antigenicity and high hydrophilicity. Collagen solution can be prepared in 0.1-0.02 M acetic acid at a concentration of 2-20% w/v. The concentration of collagen used for cell encapsulation is preferably 2%-20% w/v in complete cell growth media.

Chitosan is a naturally occurring non-mammalian cationic polymer is used for 3D cell culture. It is biocompatible and lacks immunogenicity. Chitosan has a hydrophilic surface promoting cell adhesion, proliferation, and differentiation. Chitosan can be mixed with acetic acid at a ratio of 2:1 by weight to form a homogeneous chitosan solution. The concentration of chitosan used for cell encapsulation is preferably 0.5%-10% w/v in complete cell growth media.

Once cell spheroids are formed within the microfluidic device, then can be deposited into an array of wells, microchambers, or docking stations where the cells can be monitored for viability, growth, proliferation, development, motility, intercellular interaction, and interactions with the polymer scaffold or with extracellular matrix components. A device containing the spheroids can be placed in to a typical cell culture incubator for a period of hours, days or weeks and removed periodically for monitoring. The device can be configured to fit onto a standard stage of an inverted light microscope, such as a fluorescence microscope, and the device also can optionally include a transparent window covering the incubation chamber containing the spheroids, so as to permit non-disruptive microscopic observation of the spheroids. The device also can optionally include a separate perfusion pathway to allow perfusion of the spheroids individually, collectively, or in groups with desired media containing a variety of agents. Such agents can include, for example, known or candidate antitumor agents, peptides, cytokines, antibodies, aptamers, nucleic acids, nucleotides, siRNA, antisense RNA, cell adhesion molecules or inhibitors of cell adhesion such as RGD peptides, receptor agonists or antagonists, labeled compounds such as fluorescent compounds or antibodies.

A microfluidic device according to the invention can have a number of possible configurations. Generally, however, it will include three or more inlets for the introduction of fluid into a fluid pathway or channel of the device, three or more interconnected microchannels, a nozzle for the formation of individual aqueous droplets in an oil, and an incubation chamber for the cell spheroids produced at the nozzle. The device may also include one or more outlets for removal of a fluid from the device, one or more mixing zones, one or more filters, one or more microchannels or docking stations for incubation and/or treatment of individual spheroids, and one or more perfusion channels for introduction and removal of cell culture media and/or other solutions containing agents for treatment or analysis of the spheroids. The microchambers or docking stations can be arranged in an array of 1000 or more ordered positions for monitoring and analysis. Microchambers can be essentially spherical, or cylindrical, or have a different shape. The device may also include one or more valves, pumps, vacuum channels, ports, heaters, vents, reservoirs, reagents, or waste chambers, or any combination thereof.

The flow rates required for each of the fluid inputs into the microfluidic device can vary depending on the design of the device and the concentrations of components such as the cell concentration, the polymer precursor concentration, and the polymerization mediator (e.g., calcium chloride) concentration. Exemplary flow rates are as follows. For the flow of oil into the oil inlet: 150-500 µl/hr, 150-400 µl/hr, or 200-500 µl/hr. For the flow of cell suspension into the cell inlet: 75-150 µl/hr, 75-100 µl/hr, or 100-150 µl/hr. For the flow of calcium chloride solution, 1-20 µl/hr or 1-10 µl/hr. Suitable flow rates can be readily ascertained and optimized by routine experimentation with a given device.

An important parameter used to determine the size of the cell spheroids is the size of the microchambers and connecting microchannels of the incubation chamber. The size (i.e., diameter) of the microchambers limits the size of the spheroids, and polymer scaffolds, to slightly less than that of the microchamber. Microchamber size can be, for example, any value from about 70 to about 900 microns. Docking sites are typically somewhat larger, in the range from about 600 to about 900 microns. The diameter of the microchannels is less than that of the microchambers, such as from about 50 to about 300 microns, and somewhat larger for docking site embodiments, such as about 200 to about 400 microns.

Fabrication of the microfluidic device can be by any method known in the art. A common and suitable method is to use a "soft" lithography method to pattern a template for the upper portion of the device, which is then cast from polydimethylsilane (PDMS) and peeled from the template. The PDMS portion contains the channels and other structural and fluid handling features of the device. The PDMS portion is then subjected to plasma treatment and then adhered to glass, such as a glass microscope slide. Holes may be drilled into the PDMS portion of the device as appropriate to provide inlets and outlets.

Figure 1B:
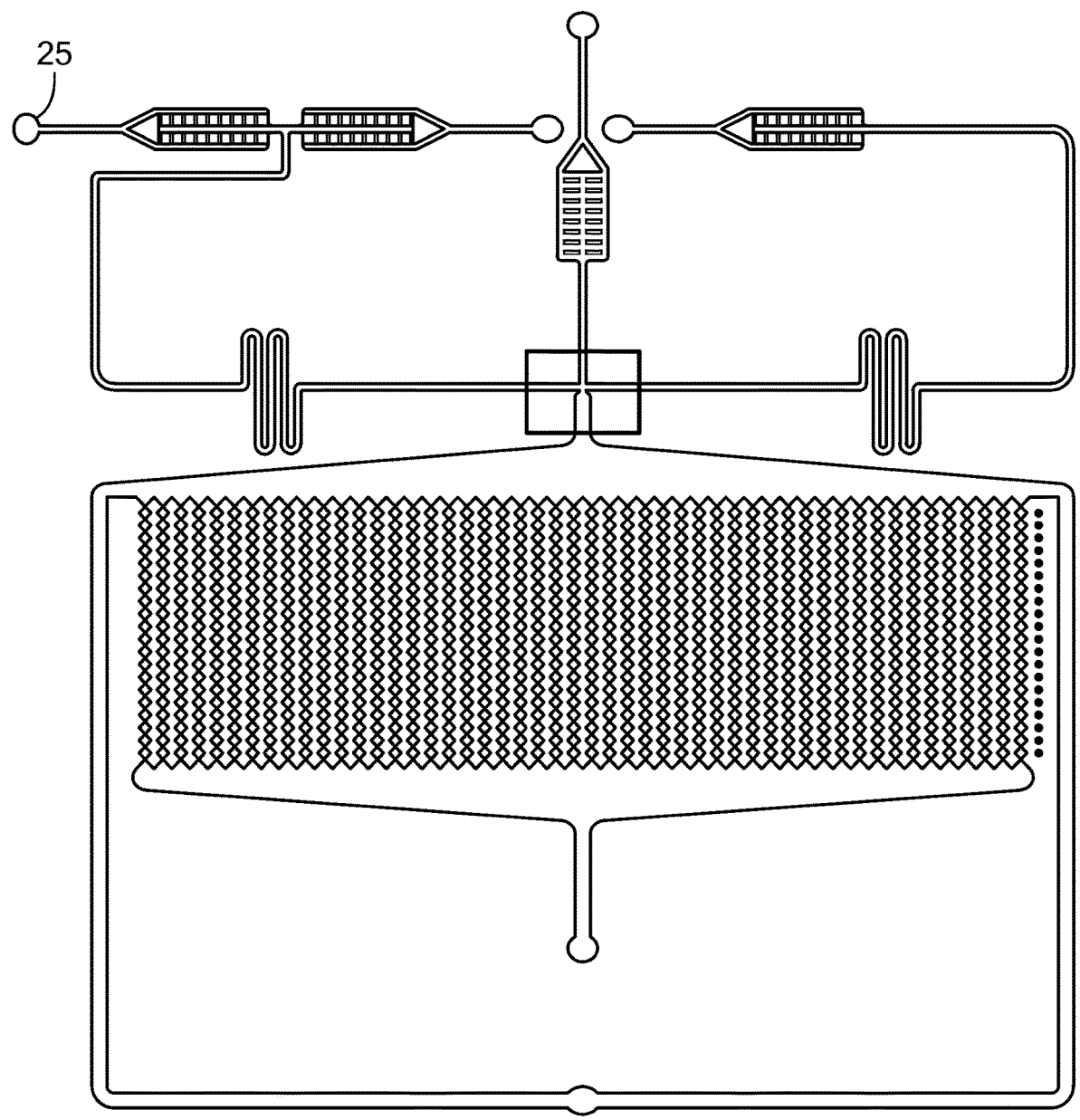
Figure 1C:
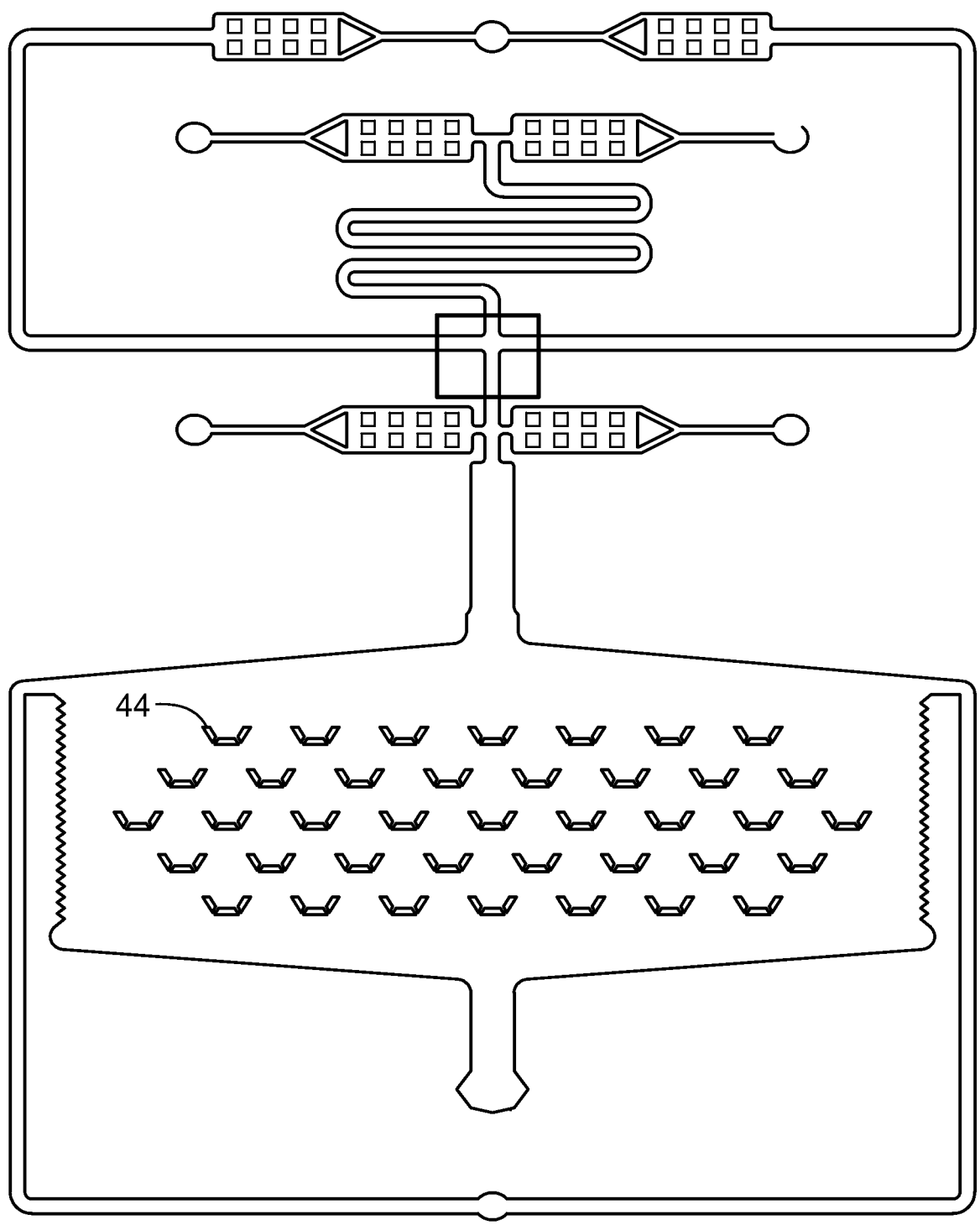

FIGS. 1A-1C describe three exemplary embodiments of the microfluidic device of the invention. In FIG. 1A, first inlet 10 is intended for the introduction of the oil phase. The first inlet is connected via a short microchannel to optional filter 12, which outputs to optional mixing zone 14, which in turn connects to nozzle 15. Second inlet 20 can be used for either a cell suspension or a calcium solution, as can third inlet 30. Both second and third inlets are connected via microchannels to optional mixing zones 24 and 34, which then are connected via microchannels to additional inputs that, together with the output of the oil microchannel, form the T-junction of the nozzle (rectangle on FIG. 1A). The intersection of three substantially perpendicular inlet microchannels forms the nozzle. The flow rates are controlled so that, in this design, the oil stream breaks the cell stream and forms aqueous droplets containing the cells and alginate, and optionally the calcium. Alternatively, the droplets can first be formed and ordered into the array, and subsequently the calcium solution is allowed to flow over the droplets in the array, causing gelation from the outside inward, forming either an encapsulating shell or a fully polymerized microbead. The output of the nozzle feeds into a collecting space 41 at the top of incubation chamber 40. The lower end of the collecting space provides a series of funnels aligned with the columns of microchambers 42, each of which will receive the droplets that cell spheroids and eventually retain a single cell spheroid. Outlet 45 at the lower end of the incubation chamber is used to collect fluid that has passed through the incubation chamber. Perfusion pathway 50 is a microchannel surrounding the incubation channel. The perfusion pathway contains perfusion inlet 55, which together with outlet 45 can be used to perfuse the microchambers and the incubation chamber.

FIG. 1B shows an embodiment that differs from that in FIG. 1A in providing second cell suspension input 25, which is used to mix two different types of cells for co-incubation in the cell spheroids. The embodiment shown in FIG. 1C has similar inputs to that of FIG. 1B, i.e., first and second cell suspension inputs, but using a different physical layout, and demonstrates that a variety of different physical layouts may be used. More importantly, the incubation chamber of the device shown in FIG. 1C provides an array of docking stations, rather than microchannels. The docking sites are intended to collect and entrap droplets that form cell spheroids, particularly larger spheroids of 600-900 microns in diameter. In this design, the oil stream breaks the two cell streams at the nozzle, and the droplets are collected at the docking sites, following which the calcium solution can flow over the droplets to gel the alginate. Cell spheroids can be on the order of about 50 to about 900 microns in diameter, such as from about 50 to about 600 microns or about 70 to about 800 microns for microchamber embodiments, and about 600 to about 900 microns for docking site embodiments.

Figure 2A:
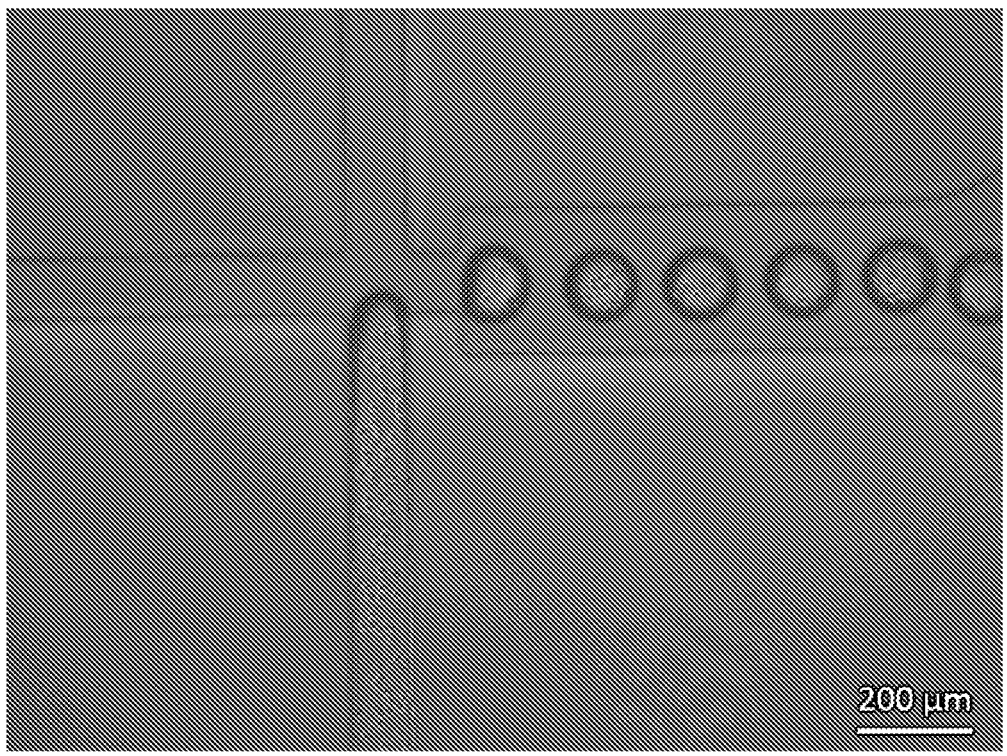
FIG. 2A is light micrograph of the nozzle area of a microfluidic device of the invention during the formation of aqueous spheres in oil.
Figure 2B:
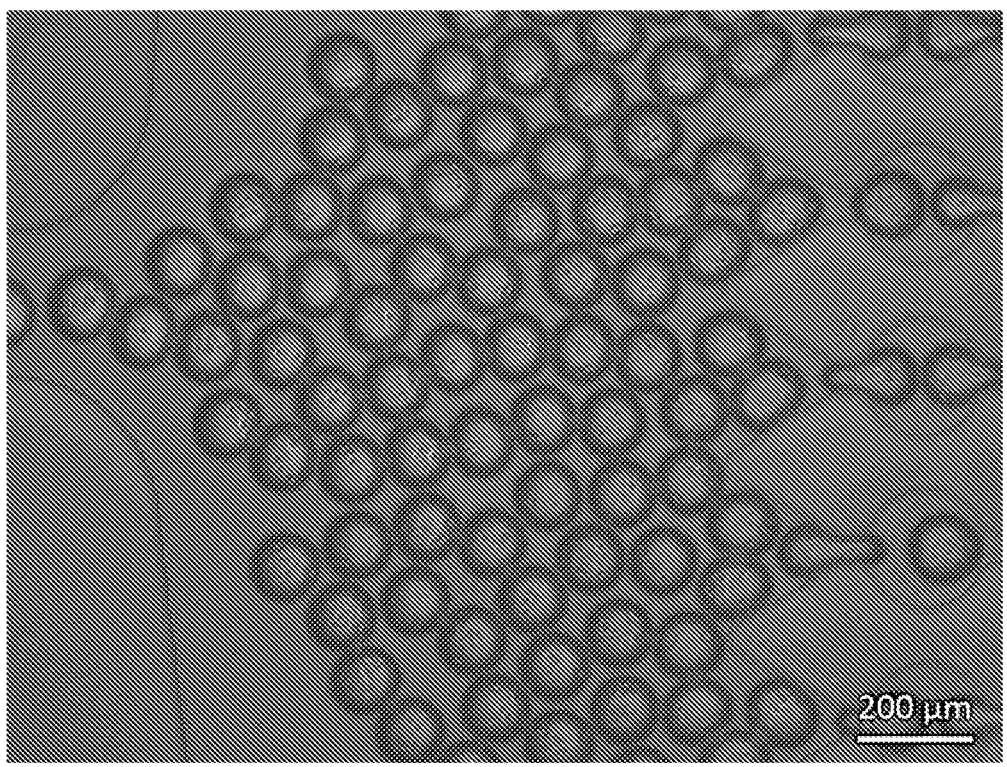
FIG. 2B is a light micrograph of the collecting zone proximal to the nozzle, showing the collection of freshly formed microspheres and their distribution into the microchannels and microchambers of the incubation chamber of the device.
Figure 3:
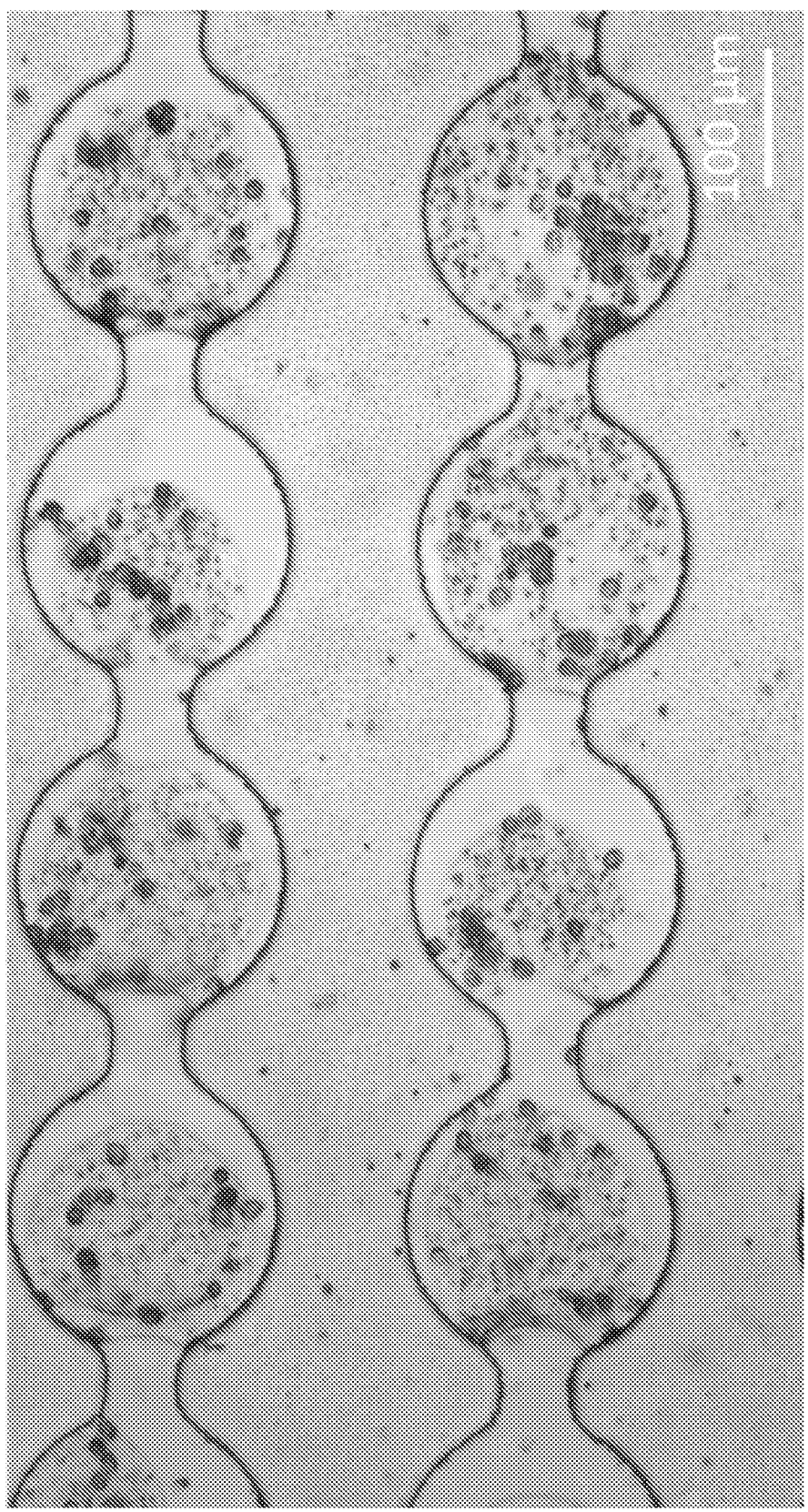
FIG. 3 shows a light micrograph of two rows of interconnected microchambers of a microfluidic device of the invention. The microchambers each contain a single microsphere of polymerized alginate and MCF7 cells.
Figure 4A:
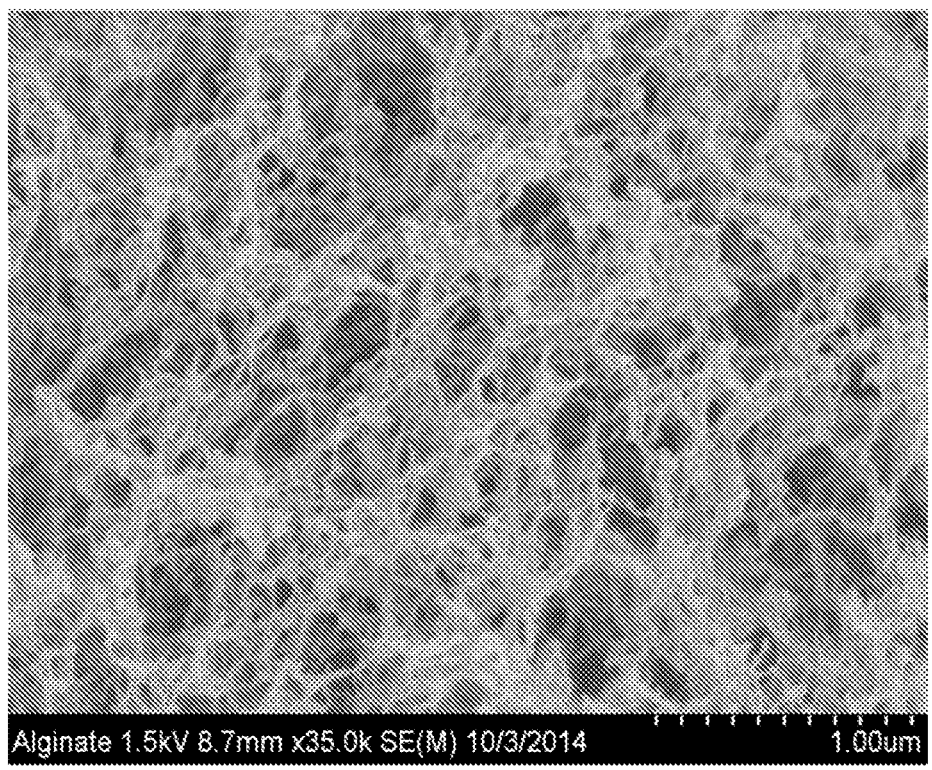
FIG. 4A shows a scanning electron micrograph (SEM) of an alginate microsphere polymerized in the absence of cells using a microfluidic device of the invention.
Figure 4B:
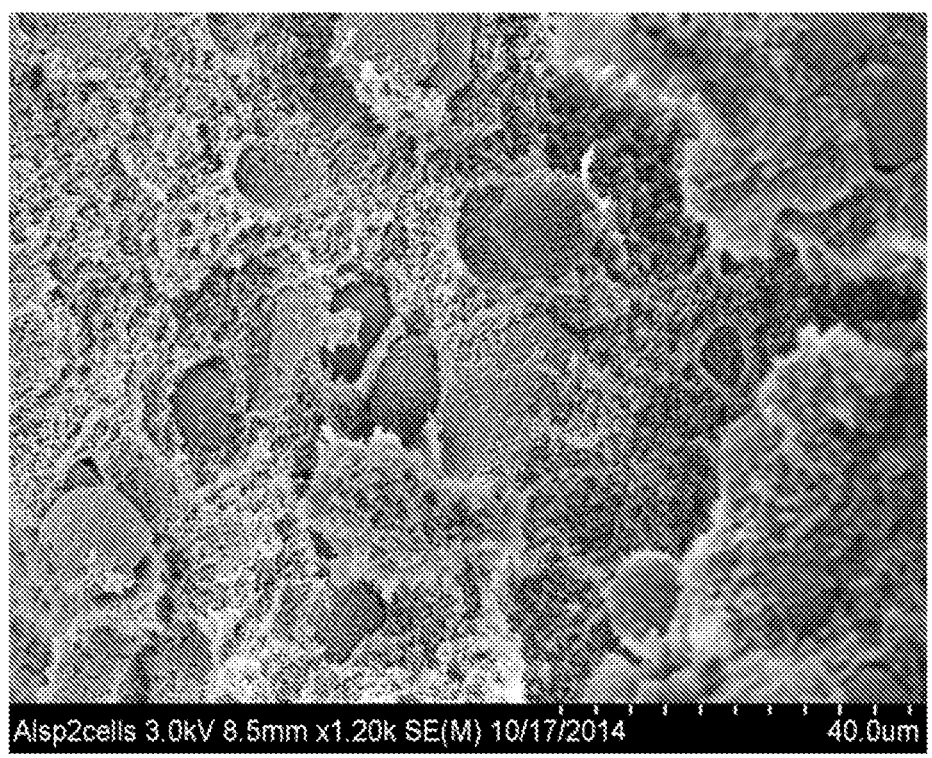
FIG. 4B shows an SEM of an alginate microsphere copolymerized with MCF7 cells using a microfluidic device of the invention.

FIG. 2A shows a light microscopic image of the nozzle area during the formation of aqueous droplets. In this example, oil is flowing in from the microchannels shown at the left and top sides of the image, and aqueous cell suspension is flowing up from below. A series of newly formed aqueous droplets immersed in the oil stream is flowing off to the right. In FIG. 2B a group of freshly formed droplets is gathered in the collection zone of the incubation chamber and is being sorted by the funnel structures on the right into the columns of microchambers connected by short microchannels. FIG. 3 shows a portion of two columns of microchambers, each of which contains a single cell spheroid (here, MCF7 cells in an alginate scaffold). FIG. 4A shows a close-up SEM image of a pure alginate scaffold formed in the microfluidic device in the absence of cells. FIG. 4B shows an SEM image of a portion of a cell spheroid containing both alginate scaffold and attached MCF7 cells.

The invention also contemplates methods of making a plurality of cell spheroids. The method includes providing an embodiment of the microfluidic device described above, together with an oil, a cell suspension comprising a polymer precursor, and optionally a polymerization mediator, if such is required to form a scaffold from the polymer precursor. The oil, cell suspension, and optionally the polymerization mediator are flowed into first, second, and third inlets of the device. The nozzle of the device forms aqueous droplets suspended in the oil. The droplets contain cells of the cell suspension, the polymer precursor, and optionally the polymerization mediator. In a variation of the method, the polymerization mediator is added subsequent to the formation of the aqueous droplets. The polymer precursor is allowed to polymerize to form polymer scaffolds in the aqueous droplets, whereby a cell spheroid is formed in each droplet. The droplets are then distributed into the microchambers of the microfluidic device. In a variation of the method, the droplets are distributed into the microchambers prior to polymerization of the polymer scaffold. In another variation of the method, the flow of oil is stopped and an aqueous solution such as a cell culture medium is flowed into the incubation chamber, whereby the cell spheroids are washed. The gelation of the spheroids can be performed either before or after this step.

After cell spheroids with scaffolds are in place in the array of microchambers or docking sites in the incubation chamber, a flow of cell culture medium can be initiated through the incubation chamber, such as by using a perfusion channel of the device. The device is then placed into an environment suitable for survival and/or growth of the cells in the cell spheroids, such as a convention incubator used for cell culture. Preferably, continuous flow of cell culture medium is maintained while the cells in the device are in the incubator. Over a period of hours to days, cells in the spheroids grow and proliferate.

The matured cell spheroids are useful for studies of a variety of agents or test substances, such as antitumor agents. The microfluidic device containing the microspheroids in the incubation chamber are perfused with an aqueous solution, such as a culture medium, containing the test substance. The cell spheroids are then monitored using a suitable technique, such as fluorescence microscopy, a cell viability assay, or other method to determine a state of interest of the cells. The microfluidic device of the invention can be used to screen different antitumor agents against the tumor cells of a particular patient, such as a human or other mammalian subject, to determine an effective agent or combination of agents for chemotherapeutic intervention for the patient. The device also can be used for basic studies of cell interactions, cell-matrix interactions, or for the development of new antitumor agents.

EXAMPLES

Example 1

Formation of Cell Spheroids in a Microfluidic Device

The microfluidic device depicted in FIG. 1A was used to prepare spheroids of MCF7 breast cancer cells. The three inlets of the device were simultaneously fed with mineral oil containing 3% v/v of Span 80 (a surfactant), a suspension of MCF7 cells at 7-10 million cells/mL and containing 2% w/v sodium alginate in Dulbecco's Modified Eagle Medium (DMEM) containing 10% v/v fetal bovine serum and 1% v/v antibiotic antimycotic solution, and a 4% w/v $CaCl_2$ solution. The solutions were introduced simultaneously into the device using syringe pumps. The flow rates were 300 µL/hr for the oil, 75 µL/hr for the cell suspension, and 10 µL/hr for the calcium solution. The size of the microchambers was 200 microns, and the average size of the cell spheroids produced was 170+/−25 microns. After the spheroids were produced, the flow of oil, cell suspension, and $CaCl_2$ solution was stopped, the incubation chamber of the device was continuously perfused with cell culture medium, and the device was placed in a cell culture incubator maintained at 37° C. and 95% air, 5% $CO_2$.

Example 2

Cell Viability

The viability of cells in cell spheroids incubated in a microfluidics device of the invention was determined using the LIVE/DEAD viability/cytotoxicity assay for mammalian cells by Life Technologies (Cat No: L-3224). The kit included two dye components: calcein-AM as an indicator of live cells and ethidium homodimer-1 as an indicator of dead cells. For live cells, calcein-AM was cleaved by esterase enzymes to form the green fluorescent dye calcein in the cytoplasm of the cells. For dead cells, the compromised cell membranes allowed ethidium homodimer-1 to permeate and bind to the nucleic acids in the nuclei of the cells, which then emitted a red fluorescence.

Figure 5:
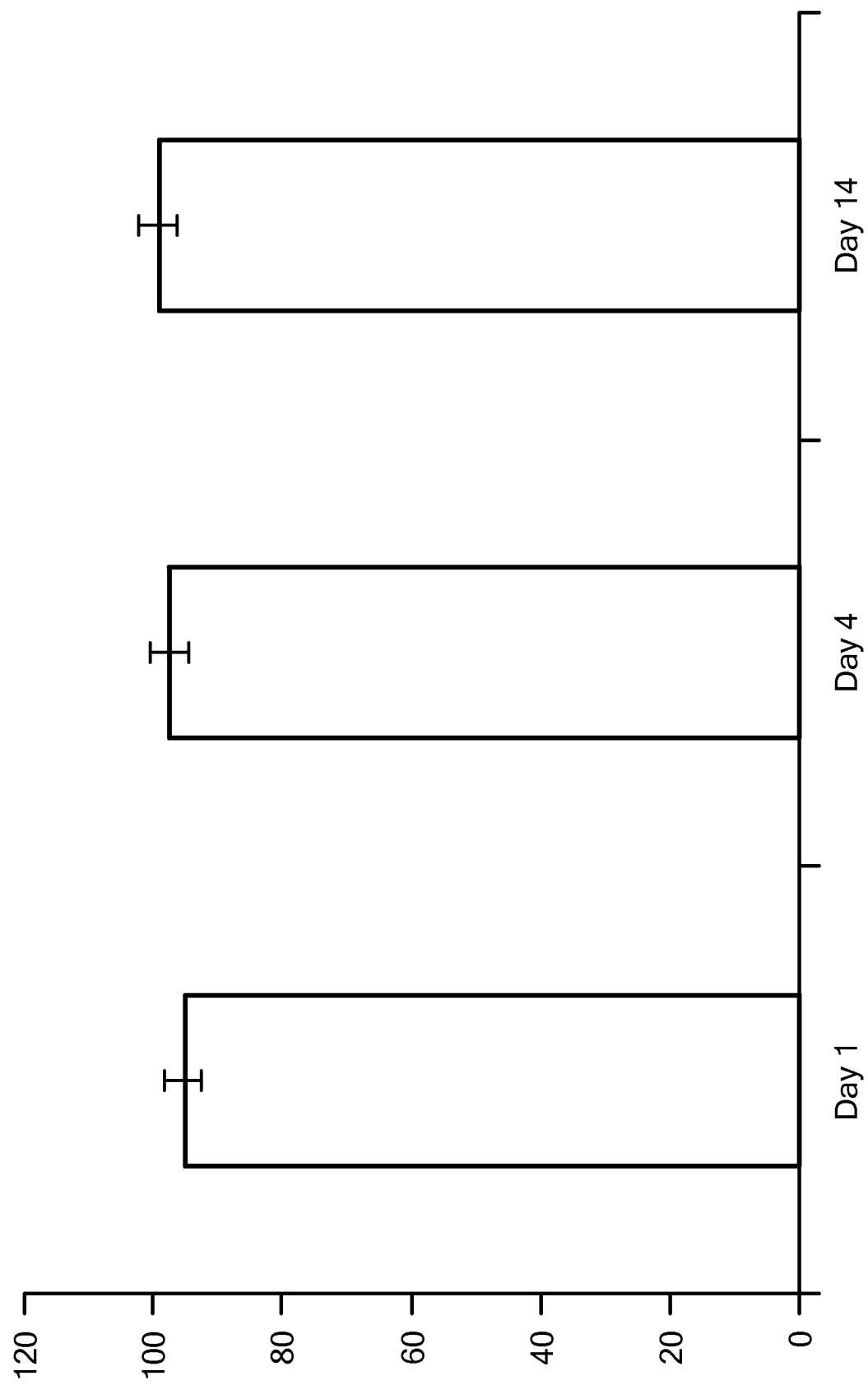
FIG. 5 shows the viability of MCF7 adriamycin sensitive 3D spheroids in a microfluidic chip over 14 days.

3D spheroids of MCF7 adriamycin sensitive cells, a breast cancer cell line, were formed in a microfluidic device of the invention as described in Example 1. The cell spheroids were housed in the microfluidic device for 14 days and continuously perfused with fresh cell culture medium, and the cell viability was checked after 1, 4, and 14 days using the LIVE/DEAD assay. As can be seen in FIG. 5, there was no statistically significant change in the cell viability over a period of 14 days, after which about 99% of the cells were alive.

Example 3

Sensitivity of Cell Spheroids to Antitumor Agents

The cell viability assay described in Example 2 was used to ascertain the sensitivity to doxorubicin of MCF7 breast cancer cells in cell spheroids present in a microfluidic device of the invention.

Figure 6A:
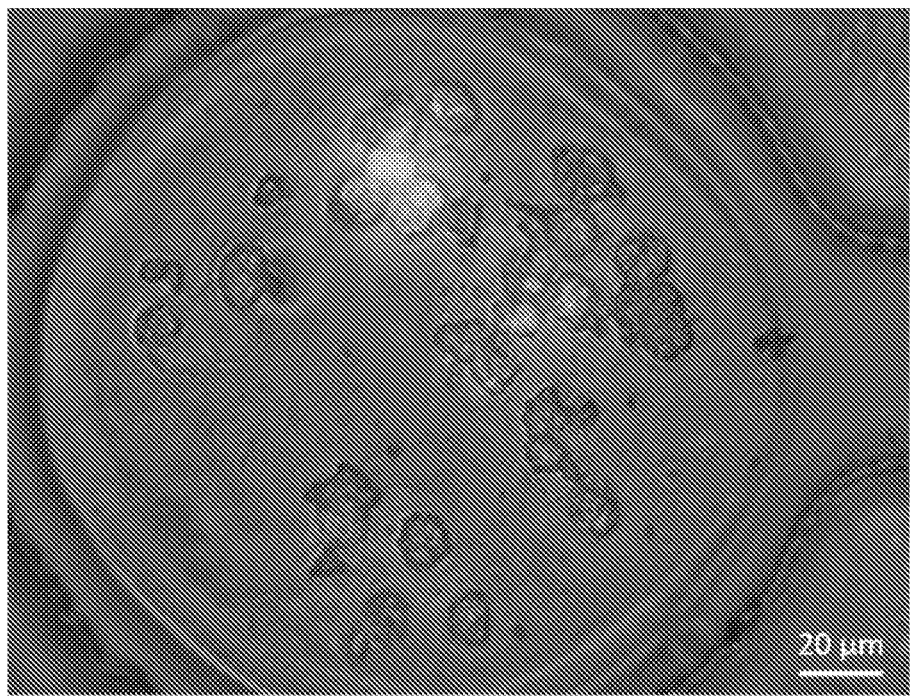
FIGS. 6A-6F show the analysis of doxorubicin effects on MCF7 cell spheroids in a microfluidic device incubation chamber.
Figure 6B:
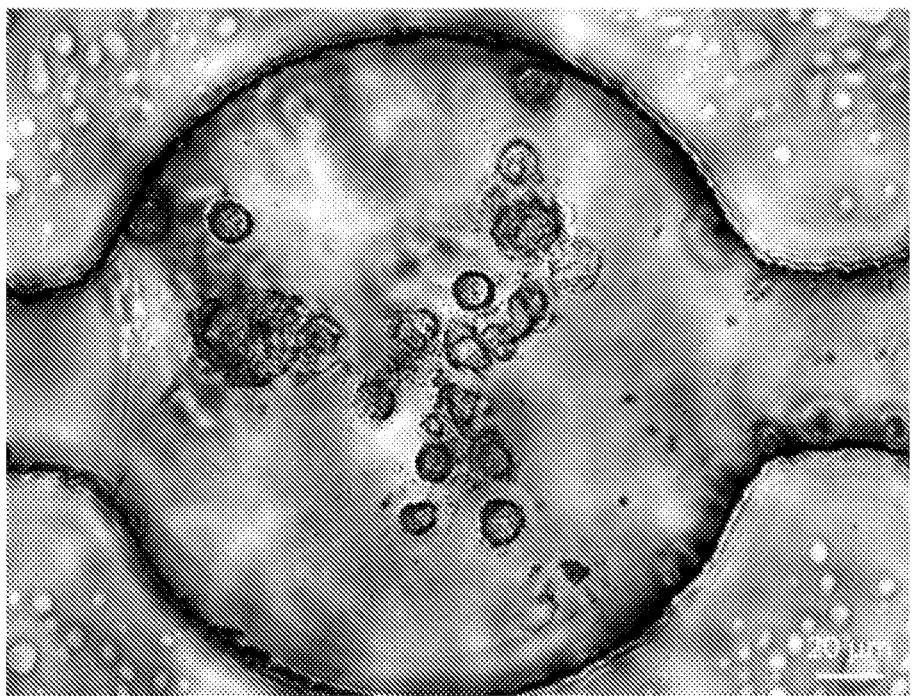
Figure 6C:
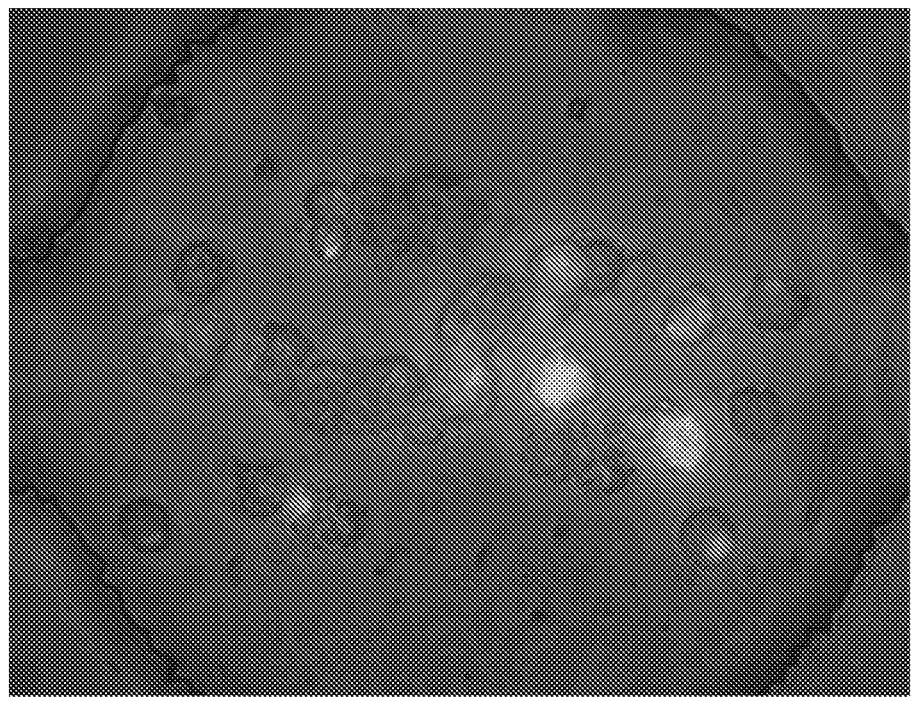
Figure 6D:
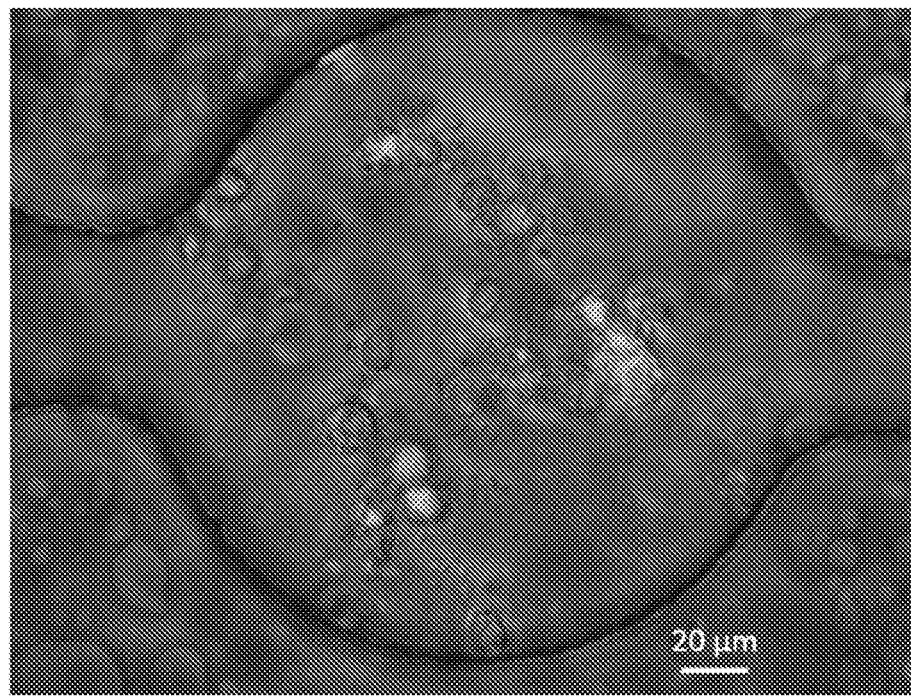
Figure 6E:
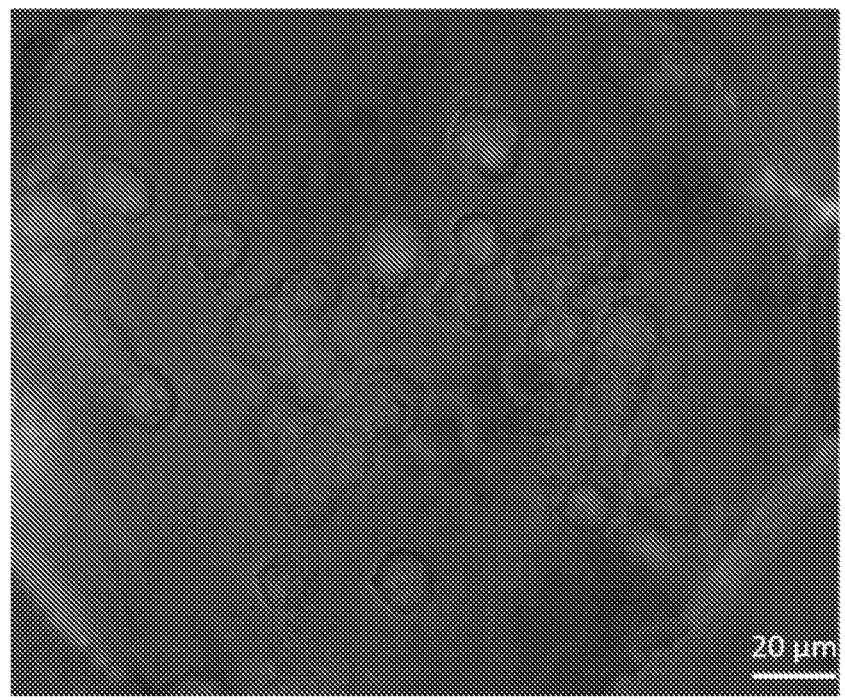
Figure 6F:
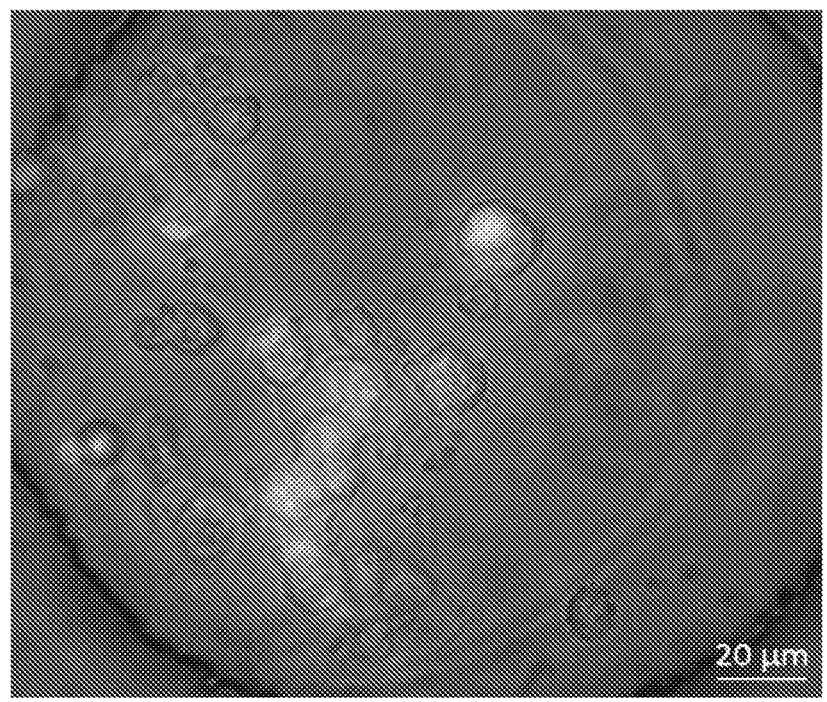

FIGS. 6A and 6B show adriamycin resistant MCF7 cell spheroids at 96 hr incubation without doxorubicin (FIG. 6A) and at 48 hr incubation with 12.8 µM doxorubicin (FIG. 6B). The red fluorescence in FIG. 6B indicates cell toxicity of the doxorubicin. FIGS. 6C and 6D show adriamycin sensitive MCF7 cell spheroids at 96 hr incubation without doxorubicin (FIG. 6C) and at 48 hr incubation with 12.8 µM doxorubicin (FIG. 6D). Comparing the red fluorescent nuclei staining in FIGS. 6B and 6D, it can be seen that adriamycin sensitive MCF7 cells were more susceptible to doxorubicin than the adriamycin resistant cells. FIGS. 6E and 6F show cell spheroids containing a mixture of adriamycin sensitive MCF7 cells and HS5 fibroblasts. FIG. 6E shows the viability result after 96 hr in the absence of doxorubicin, and FIG. 6F shows the result after 48 hr incubation with 12.8 µM doxorubicin.

Figure 7A:
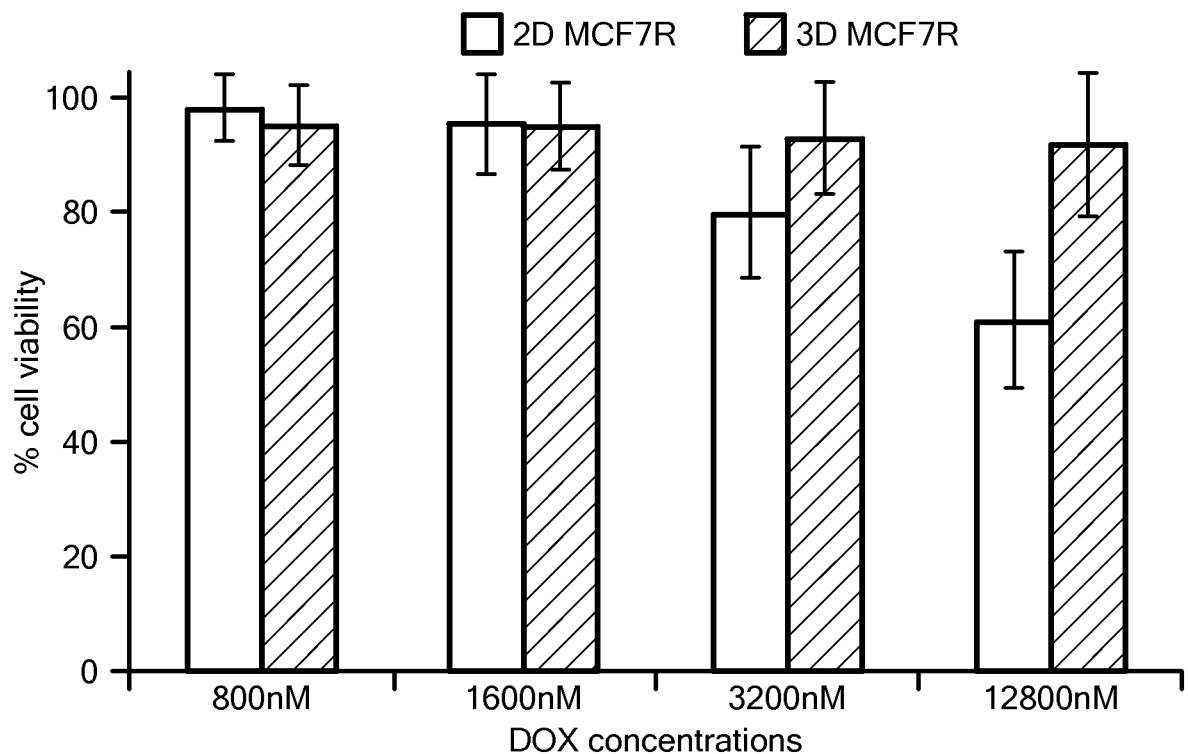
FIGS. 7A-7D compare the effect of doxorubicin on 2D cell monolayers and 3D cell spheroids containing MCF7 cells.
Figure 7B:
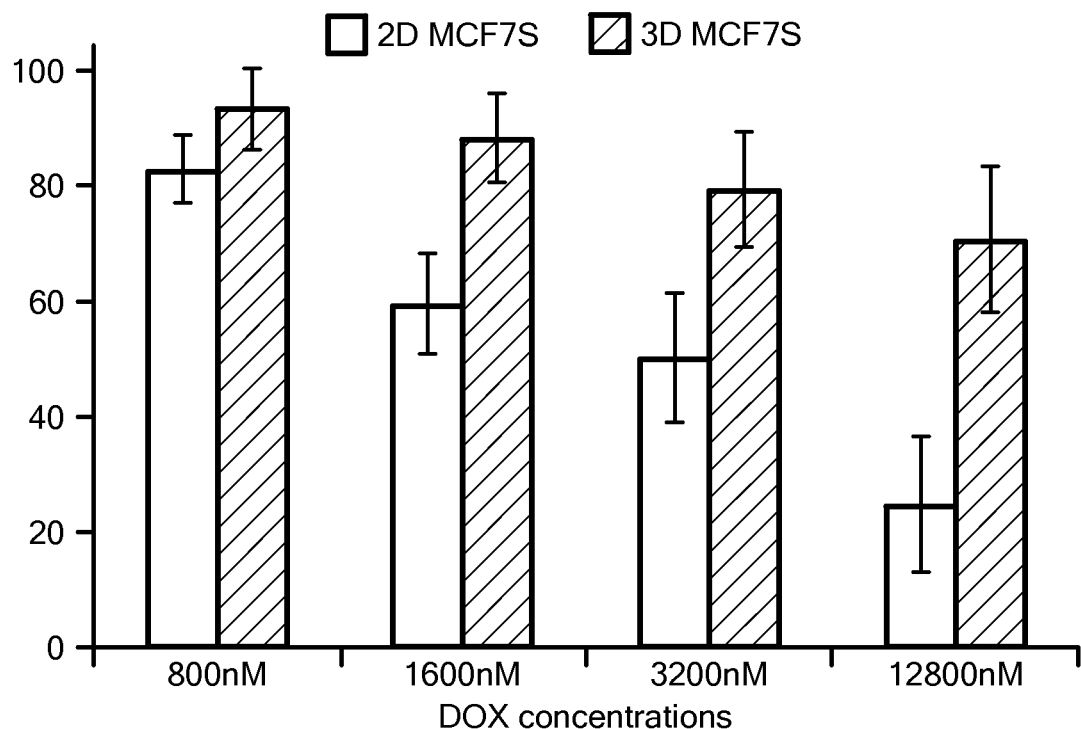
Figure 7C:
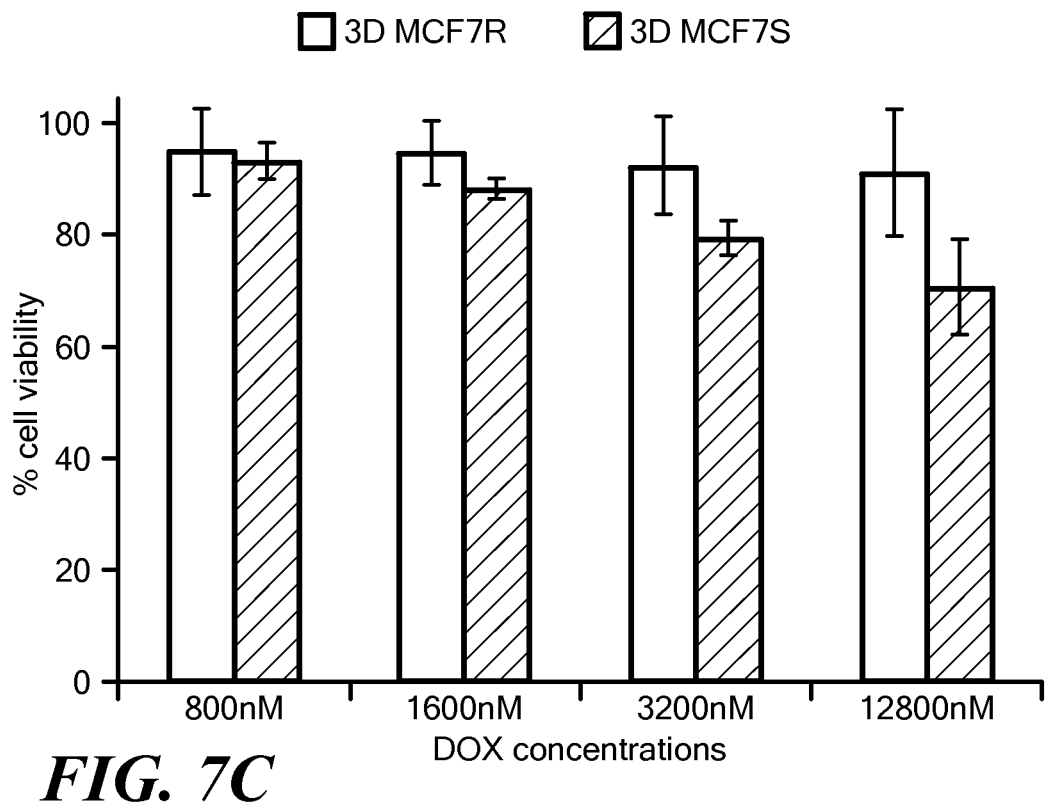
Figure 7D:
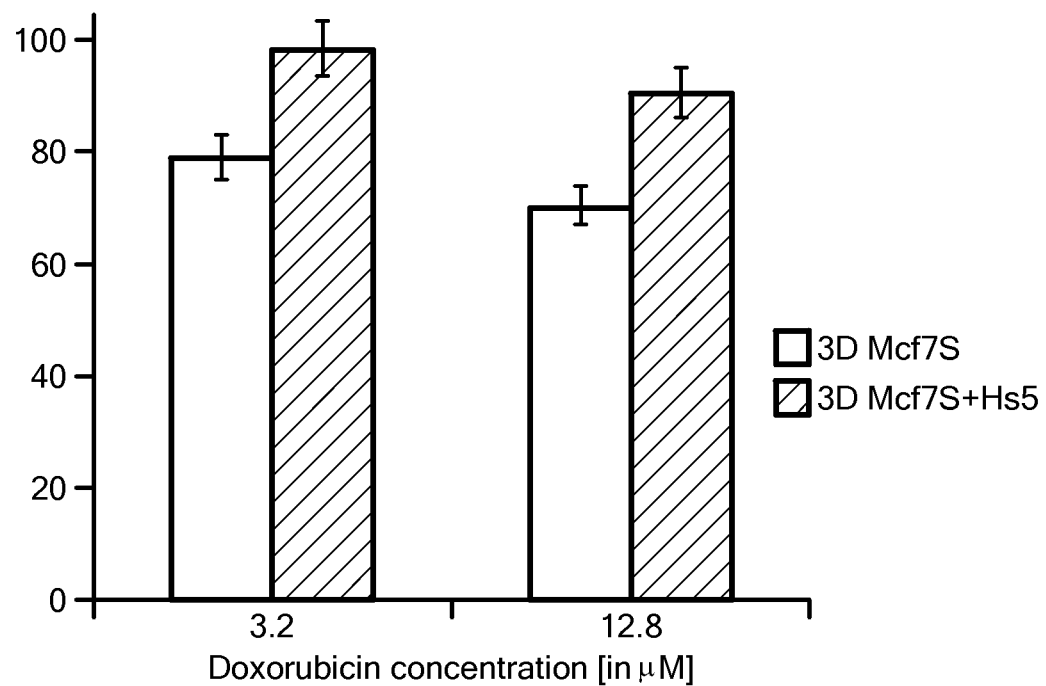

The results obtained from the viability study described above, and similar studies employing lower doxorubicin concentrations, were compared to doxorubicin sensitivity in 2D cell cultures; the comparison is shown in FIGS. 7A-7D. In FIG. 7A, it can be seen that for the 12.8 µM concentration of doxorubicin there was a statistically significant difference in cell viability ($p<0.05$) between 2D and 3D cultures, indicating that the tumor cells were more susceptible to drug treatment in a 2D environment compared to a 3D environment. Similarly, in FIG. 7B it can be seen that, for most concentrations of doxorubicin tested (from 1600 nM to 12800 nM), there was a statistically significant difference in cell viability ($p<0.05$) between the 2D and 3D cultures. As seen in FIG. 7C, the adriamycin sensitive MCF7 cells and the adriamycin resistant MCF7 cells had high and comparable survival rates in spheroids. It appears that the microenvironment and the 3D architecture of cell spheroids play an important role in protecting tumor cells from the effects of chemotherapeutic agents. In FIG. 7D, it is evident that the addition of fibroblasts, which provide a supporting cell component to the spheroid cultures, caused a significant increase in the overall cell survival rate in response to doxorubicin.

Figure 8:
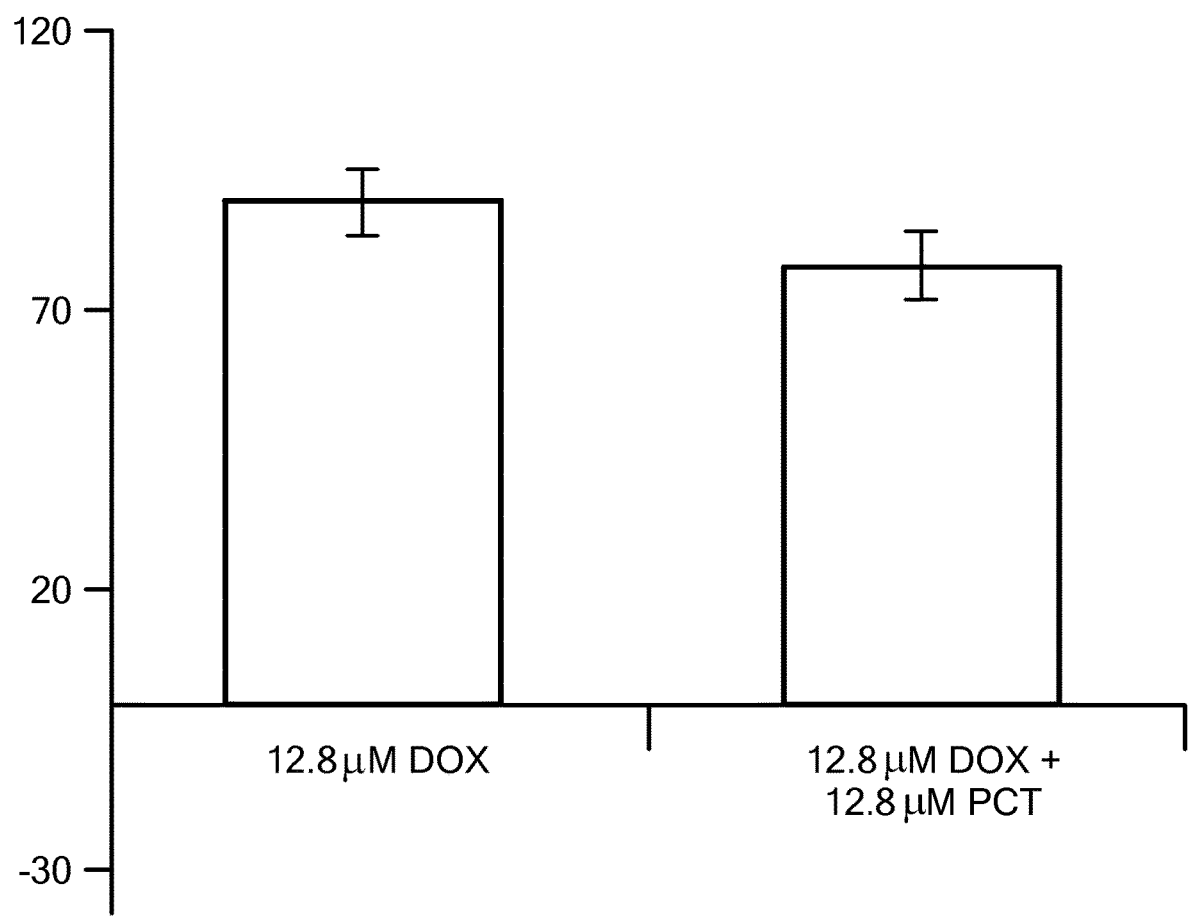
FIG. 8 shows the results of treating with different chemotherapeutic regimens in co-cultured MCF7 and HS5 cell spheroids. The co-cultured cell spheroids were incubated either with doxorubicin (DOX) along or concurrently with DOX and paclitaxel (PCT), and cell viability was determined.

The sensitivity of co-cultured MCF7 and HS5 cells to a combination of antitumor agents (i.e., 12.8 µM doxorubicin with and without 12.8 µM paclitaxel, 48 hr incubation) was also investigated. As shown in FIG. 8, there was a statistically significant drop in viability upon combination treatment as compared to the single drug treatment regimen.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

This application claims the priority of U.S. Provisional Application No. 62/017,318 filed 26 Jun. 2014 and entitled "Novel 3D In Vivo Mimicking Microenvironment to Deliver Cell Based Therapy or/end Evaluate New Therapeutics and In Vivo Cell Delivery Methods", the whole of which is hereby incorporated by reference.

The invention claimed is:

1. A method of making a plurality of cell spheroids, the method comprising the steps of:
  (a) providing a microfluidic device comprising:
  a first inlet fluidically connected to an oil, a second inlet fluidically connected to a first cell suspension comprising cells and a polymer precursor, a third inlet fluidically connected to a second cell suspension, and a fourth inlet fluidically connected to a polymerization mediator solution; the first inlet fluidically connected to a first microchannel, the second inlet fluidically connected to a second microchannel, the third inlet fluidically connected to a third microchannel; the fourth inlet fluidically connected to a fourth microchannel; wherein the second microchannel is fluidically connected to the third microchannel such that a uniform cell/polymer precursor mixture is formed under flow into a fifth microchannel, the uniform cell/polymer precursor mixture comprising cells from the first and second cell suspensions and the polymer precursor; and the first microchannel is fluidically connected to the fourth microchannel and the fifth microchannel;
  a nozzle formed by a T-shaped intersection of the first microchannel, the fourth microchannel, and the fifth microchannel, the nozzle capable of combining the oil, the uniform cell/polymer precursor mixture, and the polymerization mediator solution to form aqueous droplets suspended in the oil, the aqueous droplets comprising a mixture of polymer precursor with cells from the first and second cell suspensions and the polymerization mediator solution; and
  an incubation chamber comprising a plurality of microchambers or docking stations configured in a two-dimensional array, the incubation chamber fluidically connected to the nozzle and capable of accepting and delivering said aqueous droplets individually into said microchambers or docking stations;
  (b) flowing an oil, a first cell suspension, a second cell suspension, and a polymerization mediator into said respective inputs of the microfluidic device, whereby the first cell suspension mixes with the second cell suspension and flows into the fifth microchannel to the nozzle; aqueous droplets suspended in the oil are formed by the nozzle of the microfluidic device, the droplets comprising cells of the first and second cell suspensions mixed with the polymer precursor and the polymerization mediator solution, wherein polymerization of the polymer precursor begins upon mixing the polymer precursor with the polymerization mediator solution;
  (c) allowing the polymer precursor to polymerize to form a 3D polymer network within each aqueous droplet, whereby cells from the first and second cell suspensions are embedded in the 3D polymer network to form a mixed cell spheroid in each droplet; and
  (d) distributing the cell spheroids into the microchambers or docking stations of the microfluidic device.

2. The method of claim 1, further comprising:
  (e) interrupting the flow of oil in the cell incubation chamber of the microfluidic device and flowing an aqueous solution into the incubation chamber, whereby the cell spheroids are washed.

3. The method of claim 2, further comprising:
  (f) initiating a flow of cell culture medium through the incubation chamber; and
  (g) placing the device into an environment suitable for survival and/or growth of the cells in the cell spheroids.

4. The method of claim 3, further comprising:
  (h) allowing the cells in the cell spheroids to proliferate.

5. The method of claim 1, wherein the polymer precursor is alginate, and the first cell suspension in (a) comprises alginate at a concentration from about 0.25% w/v to about 2% w/v.

6. The method of claim 1, wherein each of the first and second cell suspensions comprises one or more of tumor cells, immune cells, and stromal cells or fibroblasts, and wherein cell spheroids formed in (c) comprise tumor cells, immune cells, and stromal cells or fibroblasts.

7. The method of claim 1, wherein the 3D polymer network comprises one or more polymers selected from the group consisting of alginate and collagen.

8. The method of claim 1, wherein the first cell suspension in (a) further comprises a cell adhesion peptide.

9. The method of claim 1, wherein the polymerization mediator in (a) is a solution containing a divalent or trivalent cation.

10. The method of claim 1, wherein the flowing of oil in (b) is at a rate in the range from about 150 µL/hr to about 500 µL/hr, wherein the flowing of first cell suspension in (b) is at a rate in the range from about 75 µL/hr to about 150 µL/hr, wherein an alginate 3D polymer network is formed in (c), and wherein the polymerization mediator is a 0.1 to 1 M calcium salt solution and its flowing in (b) is at a rate in the range from about 1 µL/hr to about 20 µL/hr.

11. The method of claim 1, wherein the incubation chamber comprises an array of docking stations, and in step (d) the cell spheroids are distributed into the docking stations.

12. The method of claim 1, wherein the cell spheroids in the incubation chamber are perfused, following step (d), with an agent selected from the group consisting of known antitumor agents, candidate antitumor agents, peptides, cytokines, antibodies, aptamers, nucleic acids, nucleotides, siRNA, antisense RNA, cell adhesion molecules, inhibitors of cell adhesion, RGD peptides, receptor agonists, receptor antagonists, labeled compounds, fluorescent compounds, and antibodies.

13. The method of claim 1, wherein the micro fluidic device comprises one or more valves, pumps, vacuum channels, ports, heaters, vents, reservoirs, reagents, waste chambers, or any combination thereof.

14. A method of monitoring a cell spheroid for the effect of a test substance, the method comprising the steps of:
  (a) performing the method of claim 1, after which the device comprises an array of cell spheroids in the incubation chamber of the device, wherein cell spheroids of the array comprise tumor cells, immune cells, and stromal cells or fibroblasts;
  (b) perfusing the incubation chamber with an aqueous solution comprising the test substance; and
  (c) monitoring the cell spheroids.

15. The method of claim 14, wherein the step of monitoring comprises determining a change in survival, growth, and/or proliferation of cells within the cell spheroids.

16. The method of claim 14, wherein the cell spheroids comprise tumor cells.

17. The method of claim 14, wherein the test substance is an antitumor agent.

* * * * *